United States Patent [19]
Mathews et al.

[11] Patent Number: 5,750,870
[45] Date of Patent: May 12, 1998

[54] PLANT GENETIC TRANSFORMATION METHODS AND TRANSGENIC PLANTS

[75] Inventors: Helena V. Mathews; Richard Keith Bestwick, both of Portland; Adolph J. Ferro, Lake Oswego, all of Oreg.

[73] Assignee: Agritope, Inc., Beaverton, Oreg.

[21] Appl. No.: 384,556

[22] Filed: Feb. 3, 1995

Related U.S. Application Data

[63] Continuation-in-part of Ser. No. 263,900, Jun. 17, 1994, abandoned.

[51] Int. Cl.$^6$ .............................. A01H 5/00; A01H 5/08; C12N 15/82
[52] U.S. Cl. ...................... 800/205; 800/DIG. 37; 800/DIG. 30; 800/DIG. 64; 800/DIG. 65; 435/69.1; 435/172.3; 435/252.3; 435/419
[58] Field of Search ............................. 800/205, 37, 32, 800/DIG. 64, 65; 435/69.1, 172.3, 240.4, 252.3, 419

[56] References Cited

U.S. PATENT DOCUMENTS

| | | | |
|---|---|---|---|
| 5,240,839 | 8/1993 | Serres et al. | 435/172.3 |
| 5,416,250 | 5/1995 | Ferro et al. | 800/205 |

FOREIGN PATENT DOCUMENTS

| | | |
|---|---|---|
| 0 290 395 | 3/1988 | European Pat. Off. . |
| 0 331 083 | 2/1989 | European Pat. Off. . |
| 0 340 197 | 4/1989 | European Pat. Off. . |
| WP 91/09112 | 12/1990 | WIPO . |
| WO 91/12249 | 12/1991 | WIPO . |
| WO 95/06741 | 3/1995 | WIPO . |

OTHER PUBLICATIONS

Cordes, S., et al., "Interaction of a Developmentally Regulated DNA–Binding Factor with Sites Flanking Two Different Fruit–Ripening Genes from Tomato," *The Plant Cell* 1: 1025–1034 (1989).

Cousineau, J.C., and D.J. Donnelly, "Adventitious Shoot Regeneration from Leaf Explants of Tissue Cultured and Greenhouse–grown Raspberry," *Plant Cell. Tiss. and Org. Cult.* 27: 249–255 (1991).

DeNovoa, C.O.Y., et al., "Comparison of In Vitro Shoot Regeneration Protocols from Rubus Leaf Explants," *New Zealand J. Crop and Hort. Sci.* 20: 471–476 (1992).

Fiola, J.A., et al., "Effect of Thidiazuron, Light Fluence Rates and Kanamycin on In Vitro Shoot Organogenesis From Excised Rubus Cotyledone and Leaves," *Plant Cell* 20: 223–118 (1990).

Fromm, M.E., et al., "Stable transformation of maize after gene transfer by electroporation," *Nature* 319: 791–793 (1986).

Graham, J., et al., "Use of the GUS Gene as a Selectable Marker for Agrobacterium–mediated transformation of Rubus," *Plant Cell Tissue and Organ Culture* 20: 35–39 (1990).

Graham, J., et al., "Plantlet Regeneration and Genetic Transformation in Soft Fruit Species," *Acta Horticulturae* 280: 517–522 (1990).

Hassan, M.A., et al., "*Agrobacterium tumefaciens*–Mediated Transformation of Several Rubus Genotypes and Recovery of Transformed Plants," *Plant Cell Tiss. and Org. Cult.* 33:9–17 (1933).

Hughes, J.A., et al., "Nucleotide sequence and analysis of the coliphage T3 S–adenosylmethionine hydrolase gene and its surrounding ribonuclease III processing sites," *Nucleic Acids Research* 15(2): 717–729 (1987).

Mathews, H., et al., "Stable integration and expression of beta–glucuronidase and NPT II genes in mango somatic embryos," *Cell Dev. Bio.* 28P: 172–178 (1992).

Mathews, H., et al., "Genetic Transformation of Red Raspberry (*Rubus idaeus* L.) with Gene to Control Ethylene Biosynthesis," *ISPMB Abstracts* (Jun. 19, 1994).

Mathews, H., et al., "Genetic Transformation of Strawberry: Stable Integration of a Gene to Control Biosynthesis of Ethylene," *In Vitro Cell. Dev. Biol.* 31: 36–43 (1995).

McNicol, R.J., and J. Graham, "Genetic Manipulation in rubus and Ribes," *Acta Horticulturae* 262: 41–46 (1989).

McNicol, R.J., et al., "In Vitro regeneration of Rubus from leaf and stem segments," *Plant Cell Tiss. and Org. Cult.* 21: 45–50 (1990).

Ozias–Akin, P., et al., "Regeneration of Transgenic Peanut Plants from Stably Transformed Embtyogenic Callus," *Plant Sci.* 93: 185–194 (1993).

Vasil, V., et al, "Herbicide Resistant Fertile Transgenic Wheat Plants Obtained by Microprojectile Bombardment of Regenerable Embryogenic Callus," *Bio/Technology* 10: 667–674 (1992).

Vysotskii, V.A., and M.T. Upadyshev, "Regeneration of Vegetative Organs by Leaf Disks and Other Explants of the Genus Rubus in Vitro," *Soviet Plant Physiol.* 39: 375–380 (1992).

Fowler, C.W., et al., "Callus Formation From Strawberry Anthers," *Hort. Res.* 11: 116–117 (1971).

James, D.J., et al., "Agrobacterium–mediated transformation of the cultivated strawberry (Fragaria X ananassa Duch) using disarmed binary vectors," *Plant. Sci.* 69: 79–94 (1990).

Jelenkovic, G., et al., "Transformation Studies of Fragaria x ananassa Duch. by TI Plasmids of *Agrobacterium tumefaciens*," *HortSci.* 21: 695 Abstract #265.

Jones, O.P., et al., "The Production of Strawberry Plants from Callus Cultures," *Plant Cell, Organ Culture* 12: 235–241 (1988).

(List continued on next page.)

*Primary Examiner*—Elizabeth F. McElwain
*Attorney, Agent, or Firm*—Susan T. Evans; Gary R. Fabian; Peter J. Dehlinger

[57] ABSTRACT

An efficient transformation system for plants has been developed that yields high transformation efficiencies and pure transgenic plants. Genomic integration of transgenes was confirmed by genomic DNA hybridization analysis. Pure transgenic plants have been successfully established in soil.

20 Claims, 14 Drawing Sheets

OTHER PUBLICATIONS

Mathews, H., et al., "Strawberry transgenics: Genetic transformation for control of ethylene biosynthesis," *8th Int. Congress on Plant Tissue and Cell Culture*, Abstract # S7-26 (1994).

Nehra, N.S., et al., "Genetic transformation of strawberry by *Agrobacterium tumefaciens* using a leaf disc regeneration system," *Plant Cell Rep.* 9: 293–298 (1990a).

Nehra, N.S., et al., "Agrobacterium–mediated transformation of strawberry calli and recovery of transgenic plants," *Plant Cell Rep.* 9: 10–13 (1990b).

Nehra, N.S., et al., "Plant biotechnology and strawberry improvement," *Adv. Strawberry Res.* 11: 1–11 (1992).

Nehra, N.S., et al., "Regeneration of plants from immature leaf–derived callus of strawberry (Fragaria x ananassa (Fragaria x ananassa)," *Plant Sci.* 66: 119–126 (1990).

Nehra, N.S., et al., "The Influence of plant growth regulator concentrations and callus age on somaclonal variation in callus culture regenerants of strawberry," *Plant Cell, Tissue, Organ Culture* 29: 257–268 (1992).

Nehra, N.S., et al., "Direct shoot regeneration from strawberry leaf disks," *J. Amer. Hort. Sci.* 114: 1014–1018 (1989).

Nyman, M., and A. Wallin, "Improved culture technique for strawberry (Fragaria x ananassa Duch.) protoplasts and the determination of DNA content in protoplast derived plants," *Plant Cell, Tissue, Organ Culture* 30: 127–133 (1992).

Nyman, M., and A. Wallin, "Transient gene expression in Strawberry (Fragaria x ananassa Duch) protoplasts and the recovery of transgenic plants," *Plant Cell Rep.* 11: 105–108 (1992).

Nogata, Y., et al., "Polygalacturonase in strawberry fruit," *Phytochemistry* 34: 617–620 (1993).

Sorvari, S., et al., "Preculture medium promotes direct shoot regeneration from micropropagated strawberry leaf disks," *HortSci.* 28: 55–57 (1993).

Uratsu, S., et al., "Relative virulence of Agrobacterium strains on strawberry," *HortSci.* 26: 196–199 (1991).

Wang, D., et al., "Somatic embryogenesis and plant regeneration from immature embryos of strawberry," *HortSci.* 19: 71–72 (1984).

Cohen, C., et al., "Efficient plant regeneration from leaf and petiole explants in red raspeberry," *91st Annual Meeting of ASHS*, abstract # 575 (1994).

Daubeny, H.A., and A.K. Anderson, "Achievements and prospects—The British Columbia red raspberry breeding program," *Horticulturae* 352: 285–293 (1993).

Donnelly, D.J., et al., "In Vitro Culture of Three Rubus Species," *Acta Horticultura* 112: 69–75 (1980).

Gingas, V.M., and B.D. Stokes, "Rubus Plant Regeneration via Asexual Embryogenesis," *HortSci.* 28: 58 (1993).

Jennings, D.L., and R.J. McNicol, "Rubus breeding—recent progress and problems," *Plant Breeding Abs.* 61: 755–758 (1991).

Mathews, H., et al., "Transformation of strawberry and raspberry for control of ethylene biosynthesis," *ISPMB abstract* # 2041 (1994).

Mathews, H., et al., "Efficient genetic transformation of red raspberry, *Rubus ideaus* L.," *Plant Cell Rep.* 14: 471–476 (1995).

McNichol, R.J., and J. Graham, "In Vitro regeneration of Rubus from leaf and stem segments," *Plant Cell, Tissue, Organ Culture* 21: 45–50 (1990).

Moore, P.P., and H.A. Daubeny, "'Meeker' red raspberry," *Fruit Var.* 447: 2–4 (1993).

Owens y De Novoa, C., and A.J. Conner, "Comparison of in vitro shoot regeneration protocols from Rubus leaf explants," *New Zealand J. of Crop and Hort. Sci.* 20: 471–476 (1992).

Owens y De Novoa, C., "Empirical evaluation of in vitro media components for cell growth and shoot regeneration from Rubus explants," *New Zealand Nat. Sci.* 19: 79–86 (1992).

Owens y De Novao, C., and A.J. Conner, "Responses of Rubus genotypes to strains of Agrobacterium," *J. Genet. & Breed.* 45: 359–368 (1991).

Perkin–Veazie, P., et al., "Physiologocal changes during ripening of raspberry fruit," *HortScience* 27: 331–333 (1992).

Welander, M., "In Vitro culture of raspberry (*Rubus ideaus*) for mass propagation," *J. Hort. Sci.* 60: 493–499 (1985).

Berthomieu, P., et al., "Routine transformation of rapid cycling cabbage (*Brassica oleracea*)—molecular evidence for regeneration of chimeras," *Plant Sci.* 96: 223–235 (1994).

Christou, P., "Morphological description of transgenic soybean chimeras created by the delivery, integration and expression of foreign DNA using electric discharge particle acceleration," *Ann. of Bot.* 66: 379–386 (1990).

Christou, P., and T.L. Ford, "Recovery of chimeric rice plants from dry seed using electric discharge particle acceleration," *Ann. Bot.* 75: 449–454 (1995).

Dong, J.Z., and A. McHughen, "Transgenic flax plants from Agro–bacterium mediated transformation: incidence of chimeric regenerans and inheritance of transgenic plants," *Plant Sci.* 91: 139–148 (1993).

Mathews, H., et al., "Transgenic plants of mustard *Brassica juncea* (L.) Czern and Coss.," *Plant Science* 72: 245–252 (1990).

Oono, Y., et al., "Effects of the over–expression of the rolC gene on leaf development in transgenic periclinal chimeric plants," *Plant Cell Physiol.* 34: 745–752 (1993).

Schmulling, T., and J. Schell, "Transgenic tobacco plants regenerated from leaf disks can be periclinal chimeras," *Plant Mol. Biol.* 21: 705–708 (1993).

Basiouny, F.M., "Ethylene evolution in strawberry (Fragaria X ananassa Duch) during fruit development," *Acta. Hortic.* 265: 363–367 (1989).

De la Plaza, J.L., and C. Merodio, "Effect of ethylene chemi–sorption in refrigerated strawberry fruit," *Acta Hortic.* 265: 427–433 (1989).

Sexton, R., et al., "Role of ethylene in the abscission and ripening of red raspberry fruit *Rubus idaeus* cv. Glen Clova," in *Cellular and molecular aspects of the plant hormone ethylene* (Pech, J.C., Latche, A., and Balague, C., eds., pp. 317–322, (1993).

Irish, V.F., "Cell lineage in plant development," *Curr. Opin. Genet. Dev.* 1: 169–173 (1991).

Poethig, S., "Genetic mosiacs and cell lineage analysis in plants," *Trends Genet.* 5: 273–277 (1989).

Stewart, R.N., "Ontogeny of the primary body in chimeral forms of higher plants," in *The Clonal Basis of Development* (Subtenly, S., and I.M. Sussex, eds., New York: Academic Press, pp. 131–160, 1978).

H. Mathews, et al., "Genetic Transformation of Red Raspberry (*Rubus ideaus* L.) with a Gene to Control Ethylene Biosynthesis," HortScience 29(5):454 (1994).

Nyman, M., et al., "Transient gene expression in strawberry (*Fragaria X ananassa Duch.*) protoplasts and the recovery of transgenic plants," Plant Cell Reports 11:105–108 (1992).

Bestwick, R.K., et al., "Reduced Ethylene Synthesis and Suspended Fruit Ripening in Transgenic Tomatoes Expressing S–Adenosylmthionine," Journal of Cellular Biochemistry, Supplement 18A, p. 98 (1994).

Picton, S., et al., "Altered fruit ripenng and leaf senescence in tomatoes expressing an antisense ehtylene–forming enzyme transgene," The Plant Journal 3(3):469–481 (1993).

Dong, J–Z, et al., "Transgenic flax plants from Agrobacterium mediated transformation: incidence of chimeric regenerants and inheritance of transgenic plants," Plant Science 91:139–148 (1993).

Pavigerova, D., et al., "Somatic embyrogenesis and Agrobacterium–mediated transformation of chrysanthemum," Plant Science 97:95–101 (1994).

Michael, M.Z., et al., "Cloning of Ethylene Biosynthetic Genes Involved in Petal Senescence of Carnation and Petunia, and their Antisense Expression in Transgenic Plants," *Cellular and Molecular Aspects of the Plant Hormone Ethlene* (J.C. Pech et al., eds.; Kluwer Academic Publishers, Netherlands) pp. 298–303 (1993).

Wagoner, W.J., et al., "Superior Regeneration and Agrobacterium Infectability of Broccoli and Cauliflower Tissues and the Identification of a Procedure for the Generation of Transgenic Plants," HortScience 27(6):132–133 (1992).

Knittel, N., et al., "Transformation of sunflower (*Helianthus annuus L.*): a reliable protocol," Plant Cell Reports 14:81–86 (1994).

Matthews, H., et al., "Efficient genetic transformation of red raspberry, *Rubus ideaud L.*," Plant Cell Reports 14:471–476 (1995).

Mathews, H., et al., "Stable integration and Expression of β–Glucoronidase and NPT II Genes in Mango Somatic Embryos," In Vitro Cell. Dev. Biol. 28P:172–178 (1992).

Radke et al. (1992) Plant Cell Reports 11:499–505.

Finnegarv et al. (1994) Bio/Technology 12;883–888.

Beachy et al. (1990) Ann. Rev. Phytopathol 28:451–474.

Klee et al. (1991). The Plant Cell 3:1187–1193.

PLANT GENETIC TRANSFORMATION METHODS AND TRANSGENIC PLANTS

This application is a continuation-in-part of U.S. Patent Application Ser. No. 08/263,900, filed 17 Jun. 1994, now abandoned, herein incorporated by reference.

FIELD OF THE INVENTION

The present invention relates to genetic transformation methods useful for the stable introduction of DNA sequences into the genomes of plants. Further the invention includes transgenic raspberry and strawberry plants.

REFERENCES

Akama, K., et al., *Plant Cell Reports* 12:7–11 (1992).

An, et al., "Binary Vectors", in *Plant Molecular Biology Manual* A3:1–19 (1988).

Ausubel, F. M., et al., *Current Protocols in Molecular Biology*, John Wiley and Sons, Inc., Media Pa.

Becker, D., et al., *Plant Mol. Biol.* 20:1195–1197 (1992).

Bellini, C., et al., *Bio/Technol* 7(5):503–508 (1989).

Basiouny, F.M., Acta Horticulturae 265:363–367 (1989).

Ceponis, M.J. and Butterfield, J.E., USDA Mktg. Res. Rpt. 996: (1973).

Cordes, S., et al., *The Plant Cell* 1:1025–1034 (1989).

Cousineau, J.C., and Donnelly, D.J., *Plant Cell Tiss. and Org. Cult.* 27:249–255 (1991).

Daubeny, H.A., and Anderson, A.K., *Acta Horticulturae* 352:285–293 (1993).

Davis, M.E, et al., *Plant Cell Tiss. and Org. Cult.* 24:115–121 (1991).

Dekeyser, R., et al., *Plant Physiol.* 90:217–223 (1989).

DellaPenna, D., et al., *Plant Physiol.* 90:1372–1377 (1989).

De la Plaza, J.L.; Merodio, C., Acta Horticulturae 265:427–433 (1989).

Dellaporta, S.L., et al., *Plant Mol. Biol. Rep.* 1:19–21 (1983).

DeNovoa, C.O.Y., and Conner, A.J., *J. Genet. and Breed.* 45:359–368 (1991).

DeNovoa, C.O.Y., *New Zealand Nat. Sci.* 19:79–86 (1992).

DeNovoa, C.O.Y., and Conner, A.J., *New Zealand J. Crop and Hort. Sci.* 20:471–476 (1992).

Dong, J.Z., and McHughen, A., *Plant Cell Reports* 10:555–560 (1991).

Dong, J.Z., and McHughen, A., *Plant Sci.* 88:61–71 (1993a).

Dong, J.Z., and McHughen, A., *Plant Sci.* 91:139–148 (1993b).

Doyle, J.J., and Doyle, J.L., *Focus* 12:13–15 (1990).

Du, S., et al., *Plant Cell Reports* 13:330–334 (1994).

El-Kazzaz, M.K.; Sommer, N.F. and Fortlage, R.J., Phytopathology 73:282–285 (1983).

Feldman, K.A., and Marks, M.D., *Mol. and Gen. Genet.* 208:1–9 (1987).

Fiola, J.A., et al., *Plant Cell* 20:223–118 (1990).

Frohman, M.A., et al., *Proc. Natl. Acad. Sci. USA* 85:8998–9002 (1988).

Frohman, M.A., in *PCR Protocol: A Guide to Methods and Applications*, p.28, Academic Press (1990).

Gamborg, O.L., et al., *Exp. Cell Res.* 50:150–158 (1968).

Garfinkel, D.J., and Nester, E.W., *J. Bacteriol.* 144:732–743 (1980).

Graham, J., et al., *Plant Cell* 20:35–39 (1990).

Graham, J., and McNicol, R.J., *Acta Horticulturae* 280:517–522 (1990).

Hamilton, A.J., et al., *Proc. Natl. Acad. Sci. USA* 88(16):7434–7437 (1991).

Hassan, M.A., et al., *Plant Cell Tiss. and Org. Cult.* 33:9–17 (1993).

Higgins, E.S., et al., *Plant Sci.* 82:109–118 (1992).

Hobbs, S.L.A., et al., *Plant Cell Reports* 8:274–277 (1989).

Hood, E.E., et al., *Transgenic Res.* 2:208–218 (1994).

Hughes, J.A., et al., *J. Bact.* 169:3625 (1987a).

Hughes, J.A., et al., *Nuc. Acid. Res.* 15:717 (1987b).

Horsten, K.H., et al., *J. Gen. Virol.* 43:57–73 (1979).

Jefferson, R.A., *Plant Mol. Biol. Rep.* 5:387 (1987).

Jefferson, R.A., et al., *Proc. Natl Acad. Sci., U.S.A.* 83:8447–8451 (1986).

Jefferson, R.A., et al., *EMBO J.* 6:3901 (1987).

Jefferson, R.A., *Nature* 342:837 (1989).

Jennings, D.L., and McNicol, R.J., *Plant Breeding Abs.* 61:755–758 (1991).

Kader A.A., In: Dale A. and J.J. Luby, eds. The strawberry into the 21st Century. Portland, Ore., Timber Press., p. 145–152 (1991).

Klein, T.M., et al., *PNAS (USA)* 85(22):8502–8505 (1988).

Kozak, M., *J. Mol. Bio.* 196:947 (1987).

Lazzeri, P.A., et al., *Theor. Appl. Genet.* 81:437–444 (1991).

Lincoln, J.E., et al., *Proc. Natl. Acad. Sci. USA* 84:2793–2797 (1987).

Lincoln, J.E., and Fischer, R.L., *Mol. Gen. Genet.* 212:71–75 (1988a).

Lincoln, J.E., and Fischer, R.L., *Plant Physiol.* 88:370–374 (1988b).

Lindsey, K., and Gallois, P., *J. Exp. Botany* 41:529–536 (1990).

Lloyd, A., et al., *Science* 234:464–466 (1986).

Lowe, J.M., et al., *Plant Cell Tiss. and Org. Cult.* 33:171–180 (1993).

Lutcke, H.A., et al., *EMBO J.* 6:43–48 (1987).

Mathews, H., et al., In Vitro *Cell Dev. Biol.* 28P:172–178 (1992).

Mathews, H., et al., *Plant Sci.* 72:245–252 (1990).

McCabe, D.E., et al., *Bio/Technology* 6:923–926 (1988).

McNicol, R.J., and Graham, J., *Acta Horticulturae* 262:41–46 (1989).

McNicol, R.J., and Graham, J., *Plant Cell Tiss. and Org. Cult.* 21:45–50 (1990).

Mertens, H., et al., *J. Gen. Virol.* 62:331–341 (1982).

Michelmore, R., et al., *Plant Cell Reports* 6:439–442 (1987).

Miki, B.L.A., et al., *Plant DNA Infectious Acrents* (Hohn, T., et al., eds.) Springer-Verlag, Wien, Austria, pp.249–265 (1987).

Moore, P.P., and Daubeny, H.A., *Fruit Var.* 447:2–4 (1993).

Murashige, T., and Skoog, F., *Physiol. Plant* 15:473–497 (1962).

Oono, Y., et al., *Plant Cell Physiol.* 35(5):745–752 (1993).

Ozias-Akins, P., et al., Plant Sci. 93:185–194 (1993).

Pawlicki, N., et al., *Plant Cell Tiss. and Org. Cult.* 31:129–139.

Perkins-Veazie, P., et al., *Hortscience* 27:331–333 (1992).

Renou, J.P., et al., *Plant Sci.* 89:185–197 (1993).

Sambrook, J., et al., in MOLECULAR CLONING: A LABORATORY MODEL, Cold Spring Harbor Laboratory Press, NY (1989).

Schmulling, T., and Schell, J., *Plant Mol. Bio.* 21:705–708 (1993).

Schuerman, P., and Dandekar, A.M., *Scientia Horticulturae* 55:101–124 (1993).

Scorza, R., et al., In Vitro *Cell Dev. Biol.* 26:829–834 (1990).

Sexton, R., et al., in CELLULAR AND MOLECULAR ASPECTS OF THE PLANT HORMONE ETHYLENE (Pech, J.C., et al., Eds.) pp. 317–322 (1993).

Shepherd, R.J., et al., in PHYSIOLOGY AND BIOLOGY OF PLANT MICROBE INTERACTIONS (Keen, N.T., et al., Eds.) American Society of Plant Physiologists, Rockville, MD, pp. 131–138 (1988).

Shimomoto, K., et al., *Nature* 338:274–276 (1989).

Sjulin, T.M. and Dale, A., *J. Amer. Soc. Hort. Sci.* 112:375–385 (1987).

Studier, F.W., et al., *J. Virol* 19:136 (1976).

Toubart, P., et al., Plant. J. 3:367–373 (1992).

Tyagi, S., et al., *Theoret. and Appl. Genetics* 78:287–292 (1989).

Van Der Straeten, D., et al., *Proc. Natl. Acad. Sci. USA* 87(12):4859–4863 (1990).

VanWordragen, M.F., et al., *Plant Sci.* 81:207–214 (1992).

Vasil, V., et al., *Bio/Technology* 10:667–674 (1992).

Visser, R.G.F., et al., *Plant Mol. Biol.* 12:329–337 (1989).

Vysotskii, V.A., and Upadyshev, M.T., *Soviet Plant Physiol.* 39:375–380 (1992).

Wolyn, D.J., and Jelenkovic, G., *Plant Mol. Biol.* 14:855–857 (1990).

Worrell, A.C., et al., *The Plant Cell* 3:1121–1130 (1991).

Wright, W.R. and Billeter, B.A., USDA Mktg. Res. Rpt. 1017 (1975).

BACKGROUND OF THE INVENTION

Red raspberries (Rubus idaeus L.) have become important temperate fruit crops. "Meeker", "Chilliwack" and "Canby" are major cultivars grown in the Pacific NorthWest (PNW) of America — one of the major producers of red raspberry in the world. Cultivar Meeker is the most widely planted raspberry cultivar in the PNW because of its high yield and resistance to diseases (Moore and Daubeny, 1993).

The potential for cultivar improvement through traditional breeding methods is limited in *Rubus* due to the heterozygous nature of the species and its severe inbreeding depression. It can take 20 to 30 years to breed a *Rubus* cultivar with a characteristic transferred from unimproved germ plasm (Jennings and McNicol, 1991).

Strawberries (Fragaria X ananassa) are an important fruit crop with worldwide production of about 2.4 million tons annually. The perishable nature of the crop contributes to significant losses to the fresh market industry (Ceponis and Butterfield, 1973; Kader, 1991; Wright and Billeter, 1975). The principal cause of post harvest losses in strawberry is gray mold (*Botrytis cinerea*), most often associated with softening, bruising and leaking of the fruit (El-Kazzaz, M.K., et al., 1983). The narrow genetic base of the cultivated strawberry (Sjulin and Dale, 1987) and its polyploid nature and heterozygosity limit the potential for improvement by traditional breeding methods.

Gene transfer technology allows introduction of new traits in proven cultivars without disrupting their otherwise desirable genetic constitutions. However, the recalcitrant nature and poor transformation rate of woody species have placed them far behind the herbaceous group in the application of gene transfer methods (Schuerman and Dandekar, 1993).

The work described herein, discloses the incorporation of heterologous genes into red raspberries, specifically, the first time generation of transgenic red raspberry cultivars Meeker, Chilliwack, and Canby. Also disclosed is the generation of transgenic strawberry cultivars Tristar and Totem.

SUMMARY OF THE INVENTION

The present invention includes a method for producing transgenic plants. In the method of the present invention, an expression vector having at least a first DNA sequence that encodes a gene encoding a selectable marker functional in plant cells is introduced into cells of a target explant. This first DNA sequence is flanked by regulatory elements effective to allow expression of the sequence in plant host cells. Further, expression of this selectable marker gene produces a gene product that confers the ability of plant cells expressing the gene to grow in the presence of a selective agent. Exemplary selective agents include hygromycin, geneticin (G418) and kanamycin. Exemplary selectable marker genes include NPTII and hpt.

In one embodiment, the expression vector is an Agrobacterium-type vector.

The expression vector is introduced into cells of a target plant tissue explant under conditions to generate transformation of explant cells. In one embodiment, the vector is introduced by co-culturing a target explant in the presence of Agrobacterium containing the vector under conditions to generate transformation of explant cells by the vector. Typically, the co-culturing is carried out in liquid for from about 1 to about 3 days. Introduction of the vector into plant cells can also be carried out by other means, including, but not limited to, the following direct transformation methods: electroporation, microinjection, and microprojectile bombardment.

The plant tissue explant can be obtained from a variety of plant tissues including, but not limited to, leaf, petiole and meristem.

Transformed explant cells are then screened for their ability to be cultured in selective media having a threshold concentration of selective agent. Explants that can grow on the selective media are typically transferred to a fresh supply of the same media and cultured again. The explants are then cultured under regeneration conditions to produce regenerated plant shoots. These regenerated shoots are used to generate explants. These explants from selected, regenerated plant shoots are then cultured on a higher concentration of selective agent. This iterative culture method is repeated until pure transgenic explants are obtained.

In one embodiment, pure transgenic explants are identified by dividing the regenerated plant shoots into explants, culturing the explants, and verifying that the growth of all explants is resistant to the highest concentration of selective agent used. That is, in the presence of selective agent there is no necrosis or significant bleaching of the explant tissue.

When pure transgenic explants are verified, transgenic plants are produced by regenerating plants from the pure transgenic explants.

The vectors used in the method of the present invention may also include further DNA coding sequences, for example, a second DNA sequence which is flanked by regulatory elements effective to allow expression of the sequence in plant cells. This second DNA sequence can encode any number of useful gene products including products useful to increase fruit sugar content, increase plant/fruit fungal resistance, increase plant/fruit viral resistance, and effective to reduce ethylene biosynthesis in fruit from the plant.

Regulatory elements for use in the practice of the method of the present invention typically include transcriptional and translational initiation/termination signals. In one embodiment, the transcription regulatory elements include tissue or stage specific promoters, for example, tomato E4 (or E4-like) and tomato E8 (or E8-like). Promoters similar to, for example, the E4 promoter can be identified for a plant of interest in order to employ a promoter system homologous to the explant cell type (e.g., tomato promoters in tomato, raspberry promoters in raspberry, strawberry promoters in strawberry). Heterologous promoters are useful as well (e.g., tomato-derived promoters in transgenic raspberries or in transgenic strawberries).

In one embodiment, the method of the present invention has been applied using explants from fruit-bearing plants, such as raspberry and strawberry. Transgenic plants can be isolated using the methods and materials described above. Accordingly, the invention further includes transgenic plants and products thereof, including transgenic fruit. Several embodiments of the present invention are as follows: transgenic red raspberry plants, transgenic red raspberries, transgenic strawberry plants, and transgenic strawberries.

The transgenic fruit of the present invention can embody many modifications, including, but not limited to, increased sugar content, increased fungal resistance, increased viral resistance, and reduced ethylene biosynthesis. In one embodiment, reduced ethylene production is achieved by production, in the transgenic fruit, of a product effective to accomplish such a reduction. Such products include, for example, S-adenosylmethionine hydrolase, aminocyclopropane-1-carboxylic acid (ACC) deaminase, ACC oxidase antisense molecule, ACC synthase antisense molecule, ACC oxidase cosuppression molecule, and ACC synthase cosuppression molecule.

These and other objects and features of the invention will be more fully appreciated when the following detailed description of the invention is read in conjunction with the accompanying drawings.

DETAILED DESCRIPTION OF THE INVENTION

I. DEFINITIONS

Figure 1:
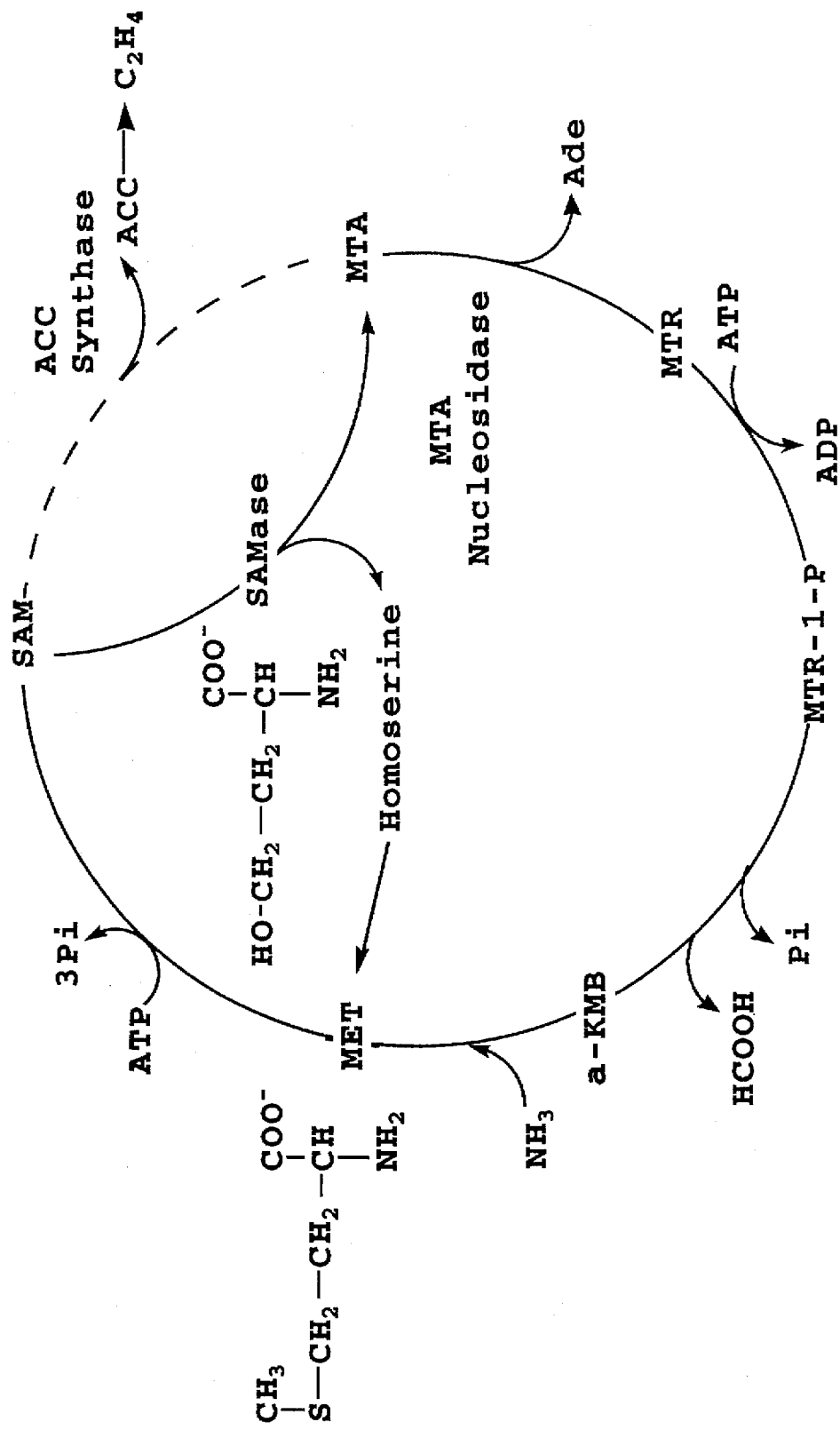
FIG. 1 illustrates the effect of SAMase expression on the methionine recycling pathway in plants.

"Red raspberry" refers to the species Rubus idaeus L.

"Strawberry" refers to the species Fragaria X ananassa.

"Transformed explant" is explant tissue containing a mixture of transformed and non-transformed cells. Compare to "non-chimeric transgenic explant."

"Pure transgenic explant" or "Non-chimeric transgenic explant" is a plant that contains essentially only transformed cells, determined as follows. Explants with transformed cells are regenerated in the presence of a selection agent to form regenerated shoots. The regenerated shoots are divided into explants and the explants cultured under selective conditions. If part of the explant tissue is susceptible to the effects of the selective agent, the explant tissue is considered to be chimeric, i.e., containing both transformed and non-transformed cells.

Sensitivity to the selective agent is typically manifest by necrosis or bleaching of tissue excised from shoot regenerants where the excised tissue is grown under selective pressure. Leaves, petioles, nodal and meristem segments of shoot regenerants are routinely tested. On the other hand, if no susceptible tissue is detected, then the source tissue is considered to be non-chimeric or pure transgenic.

"Pure transgenic plant" or "Non-chimeric transgenic plant" are plants regenerated from non-chimeric or pure transgenic explants.

"Plant shoots" are the first plant-like structures that outgrow from explant tissue cultured under regeneration conditions. The outgrowth is typically from a small number of cells present in the explant.

"Threshold concentration of selective agent" varies depending on the selective agent used and is determined by experimentation. The threshold concentration is the concentration of the selective agent that permits the growth of transformed cells carrying the selection gene, but which also allows either very low level (background growth) or no growth of non-transformed cells. The threshold concentration is typically the lowest concentration of selective agent that significantly inhibits the growth of non-transformed cells.

"Functional gene" is any gene introduced into plants that can express its encoded sequences and produce the expected gene product, such as an RNA or protein, in the plant cells in which it resides.

"E4 promoter" as used herein is any promoter or regulatory sequence derived from a gene homologous to a tomato E4 gene.

II. TRANSFORMATION METHOD

The present invention includes an improved method for the generation of transformed plant cells and pure transgenic plants.

In the method of the present invention, a suitable expression vector is selected for introduction into the cells of the target explant. The expression vector typically has at least one DNA sequence that encodes a gene encoding a selectable marker functional in plant cells. Such selectable markers are known to those of skill in the art and include the hpt gene (which confers resistance to the antibiotic hygromycin; Klebsiella sp.), and the nptII gene (originally obtained from TN5, having broad host range, conferring resistance to geneticin and kanamycin).

Expression of the selectable marker is typically under the control of a promoter that functions constitutively in plant cells (e.g., Pnos). Expression of the selectable marker gene produces a gene product that confers the ability of plant cells expressing the gene to grow in the presence of a selective agent (e.g., hygromycin).

Plant explants are typically the target of transformation. The expression vector can be introduced into the explant cells by a number of methods including electroporation, microinjection, and microprojectile bombardment. These methods are well known in the art (Klein, et al.; Miki, et al.; Bellini, et al.) and provide the means to introduce selected DNA into plant genomes.

In a preferred embodiment, the expression vector is an Agrobacterium-based vector and the transformation of the explant cells is carried out by co-culturing the explant in the presence of Agrobacterium carrying the expression vector. Numerous such Agrobacterium based vector systems are available to one of ordinary skill in the art (e.g., An, et al., 1988; Becker, et al., 1992). The use of one type of binary vectors in the practice of the present invention is described below in the Materials and Methods section.

Co-culturing of the explant and vector-bearing bacteria is typically carried out in liquid culture, under the conditions described below, for about 1 to 3 days. The concentration of the Agrobacterium in co-cultivation is typically between about $10^8$ to about $10^9$ transformed bacterial cells/ml of culture. In the examples described below the concentration is usually about $0.5-0.6 \times 10^9$.

After transformation of explant cells, the transformed explant cells are screened for the presence of the selectable marker gene by culturing the transformed explants in selective media having a threshold concentration of selective agent.

In the practice of the present invention, the ability of explants to regenerate is empirically evaluated. Having a robust regeneration system provides the maximum opportunity to recover transgenic plants from transformed explant cells. Some factors affecting regeneration ability include, but are not limited to, the following: media composition, hormone levels, concentration of selective agent, light levels, number of transfers to new culture media.

The ability to obtain regenerates from explants is maximized for the plant cells that are the selected transformation target. Different tissue explants may be transformed and the different tissues may require different regeneration conditions. In the method of the present invention, shoots, leaf, meristem and petiole explants were routinely used. For red raspberry, petiole explants appeared to provide better callus production and shoot regeneration (Example 1, Table 1). For strawberry, leaf, meristem and petiole explants all provided good callus production and shoot regeneration.

One aspect of the present invention is the application of an iterative culture/selection method. In this method, when transformed explants demonstrate the ability to grow on selection medium they are typically regenerated to form plant shoots, tissue explants isolated from the regenerated shoots, and the resulting explants grown on selection media at a higher concentration of selective agent than was present in the initial selection medium. The iterative culture selection method is continued providing increasingly stringent selection levels.

As described above, the threshold concentration of selective agent is determined. Typically, the first round of the iterative selection method is carried out at twice the threshold concentration, the second round at three times the threshold concentration, and so on. Any step-wise increase in selective agent concentration can be used, for example, 1X, 1.5X, 2X, 2.5X threshold concentrations.

Selective agent concentration is cultivar dependent and often explant tissue type dependent. In raspberry, for example, (Example 1) transformed explants of cv. Canby were subjected to geneticin selection as follows: petiole explants started at 5 mg/l went to 10, 15 then 20 mg/l, and leaf explants started at 10 mg/l and went to 15, 20, then 25 mg/l. Selective agent concentrations are typically in the range of 1–500 mg/l, but are, of course, dependent on the agent, explant-type, and selectable marker used.

In another example, (Example 10) transformed strawberry explants of cv. Tristar were cultured in regeneration medium containing either 0,10 or 25 mg/l kanamycin, followed by transfer to medium containing 50 mg/l, then subsequent transfer to medium containing 75 mg/l kanamycin.

The iterative culture method is repeated until pure transgenic explants are obtained. Pure transgenic explants are defined above. Briefly, a transformed explant that is the product of iterative selection is encouraged to undergo tissue regeneration, for example, by culturing the explant on shoot regeneration/proliferation medium. Explants are derived from the regenerated shoot(s), typically from leaf, meristem, nodal and petiole tissue. All explant tissues are cultured on media usually containing the highest level of selective agent used in the iterative selection method.

The transgenic tissue is determined to be pure if all of the explants from regenerated shoots are maintained on the selective medium and show no signs of necrosis or bleaching (extreme loss of chlorophyll).

When a pure transgenic explant is identified, the explant is regenerated to produce pure transgenic plants. The plants are then typically set in soil and allowed to mature for further evaluation.

Transgenic tissue is also evaluated by standard recombinant techniques to demonstrate the presence of the introduced genes (e.g., genomic DNA (Southern) hybridization analysis — Materials and Methods and Examples 3, 8 and 11).

In practicing the method of the present invention, the concentration of the selective agent in the first round selection should be carefully selected to allow growth of the transformed cells, and typically low level or background growth of some non-transformed cells. From this initial selection, the explant is usually subjected to shoot regeneration, leaf and petiole reselection, followed by a step-up selection (i.e., increased concentration of selective agent). Callus development ensues. The callus is usually transferred to a new medium and then transferred to another step-up concentration of selective agent. Once again, shoot regeneration is carried out and the above procedure repeated at higher concentrations of selective agent.

As an initial test of the purity of the transgenic, after shoot proliferation, leaf tissue is chopped up and placed in selection media. If part of the leaves are susceptible to the effects of the selection media (e.g., necrosis or bleaching), then the tissue is likely not pure.

In addition to the selectable marker sequences, vectors used in the method of the present invention typically have at least one second DNA sequence that encodes a functional gene. The functional gene is flanked by regulatory elements effective to allow expression of the sequence in plant cells (e.g., transcription initiation/termination signals, translation initiation/termination signals).

Gene products which may be useful to express include functional genes encoding (i) products affecting flavor or color modification proteins (e.g., sucrose phosphate synthase, which may result in increased sugar content of fruit, (Worrell, et al., 1991), (ii) products influencing plant and/or fruit fungal resistance (Toubart, et al., 1992), (iii) products influencing plant resistance, (iv) enzymes, such as encoded by the taumatin gene, and (v) products that affect ethylene production, such as anti-sense or enzymes (e.g., aminocyclopropane-1-carboxylic acid (ACC) deaminase, ACC oxidase antisense molecules, ACC synthase antisense molecules, ACC oxidase cosuppression molecules, and ACC synthase cosuppression molecules).

For example, in one embodiment of the present invention, a gene useful for the reduction of ethylene production is introduced into plants. One approach to reduce ethylene biosynthesis in plants and fruit utilizes a gene that encodes the enzyme S- adenosylmethionine hydrolase. This approach is described herein and in a co-owned, allowed U.S. Patent Application Ser. No. 08/255,833, filed 8 Jun. 1994, herein incorporated by reference, and in U.S. Application Ser. No. 08/046,583, filed 9 Apr. 1993, herein incorporated by reference.

The enzyme S-adenosylmethionine hydrolase, encoded by the E. coli bacteriophage T3, hydrolyses S-adenosylmethionine (SAM) to homoserine and 5'-methylthioadenosine (MTA) (FIG. 1).

The enzyme is known by its recommended name, AdoMet hydrolase (AdoMetase), or by its other name, S-adenosylmethionine cleaving enzyme (SAMase) (Studier, et al., 1976). Both products of the reaction (i.e., homoserine and MTA) are recycled to methionine; MTA as previously shown (FIG. 1) and homoserine via a metabolism pathway known to exist in plant tissues.

The AdoMetase gene has been identified, isolated, cloned, and sequenced from bacteriophage T3 (Hughes, et al., 1987a; Hughes, et al., 1987b; Studier, et al., 1976). Other bacteriophages that encode the AdoMetase or SAMase genes are coliphage BA14, Klebsiella phage K11, and Serratia phage IV (Mertens, et al.; Horsten, et al.).

Different bacteriophages may be expected to contain AdoMetase genes with variations in their DNA sequences. The isolation of AdoMetase coding sequences from bacteriophage coding sequences can be accomplished as previously described for AdoMetase from bacteriophage T3. Alternatively, degenerative hybridization probes for AdoMetase coding sequences can be generated and used to screen plasmids carrying fragments of a selected bacteriophage's genome for the presence of homologous sequences. AdoMetase enzymatic activity can be evaluated by standard biochemical tests.

To increase the translational efficiency of the AdoMetase gene in plants, site directed mutagenesis of the nucleic acid sequences surrounding the ATG start codon was performed. The net effect of the substitutions change the CAC-CAAATGA in the native T3 sequence to GCCACCATGG which is an optimal eukaryotic translational initiation sequence (Kozak, et al.; Lutcke, et al.).

The change also introduces an NcoI site at the SAMase start codon which facilitates fusions to different promoters.

The only alteration to the AdoMetase coding sequence is the amino acid at amino acid position two which is changed from isoleucine to valine: this is a highly conservative amino acid change. The altered form of AdoMetase was named SAM-K (SEQ ID NO:1 and SEQ ID NO:2).

Previously described experiments (U.S. Applications 08/255,833 and 08/046,583), using transgenic plants expressing an AdoMetase gene and monitoring ethylene production, have demonstrated that the effect of AdoMetase on the pathway is to "short circuit" the branch that produces ethylene: ethylene production is reduced in such transgenic plants, including production in leaf tissue and fruit.

The regulatory regions used to guide expression of gene products can also be obtained from a number of sources. Both constitutive and regulatable promoters are useful in the practice of the methods of the present invention. A tissue or stage specific promoter is a region of DNA that regulates transcription of the immediately adjacent (downstream) gene to a specific plant tissue or developmental stage of the plant or plant tissue. One exemplary regulatable promoter is the tomato E4 gene promoter (tomato E4 gene, SEQ ID NO:4 and SEQ ID NO:5; tomato E4 gene promoter/ Adometase, SEQ ID NO:6 and SEQ ID NO:7; Materials and Methods). Expression of the E4 gene has been shown to be induced (i) at the onset of ripening, and (ii) by treatment of tomatoes with ethylene (Lincoln, et al., 1987; Lincoln and Fischer, 1988a, 1998b; DellaPenna, et al., 1989). The E4/Adometase gene construct has been introduced into transgenic raspberries and into transgenic strawberries using the methods of the present invention (see below).

The methods of the present invention are applicable to all higher plants, and particularly to fruit-bearing plants. The E4 promoter, and/or the transformed plant, may be selected from a variety of plants, including fruit-bearing plants, such as tomato, eggplant, legumes, raspberry, strawberry, melon, avocado, cherry, apricot, citrus fruits, etc.; flowers, such as roses and carnations; and vegetables, such as cauliflower, and lettuce.

Regulatable promoters other than the E4 promoter can also be used in the practice of the present invention and include, but are not limited to the following: the E8 gene promoter from tomatoes (SEQ ID NO:3); polygalacturonase gene promoter from tomato; and the promoter for ethylene forming enzyme (EFE) from tomatoes. It is useful to restrict expression of some genes to specific tissues, such as the fruit — for example, any gene that would be deleterious to the plant if it were expressed constitutively. Such genes would include genes which encoded degradative enzymes that deplete necessary metabolites.

Further, the tomato genes E4 and E8 can be used as hybridization probes against libraries of DNA representative of the genomes of other plant species. Identification of homologous genes allows the identification of the regulatory sequences adjacent the homologous gene. Such regulatory sequences (e.g., a promoter region) are then tested for tissue specific expression in the plant species from which they were isolated.

Using hybridization screening methods, an E4 homologue gene in raspberries has been identified (SEQ ID NO:8 and SEQ ID NO:9). Using primers derived from these sequences, both the three and five prime ends of the raspberry E4 gene are isolated using the PCR rapid amplification of cDNA ends (PCR-RACE) reaction (Frohman, 1988, 1990), thus providing raspberry-derived promoter regions.

Additional raspberry E4 gene sequences were obtained by further hybridization screening of raspberry genomic library clones. The sequence of a genomic copy of a raspberry E4 gene is presented in SEQ ID NO:10 (nucleotide sequence) and SEQ ID NO:11 (polypeptide sequence).

Such promoters, as well as the E4 promoter itself, can be tested for regulatable expression in heterologous plant systems using the methods described herein. A reporter gene, such as uidA (Jefferson, et al., 1986), which encodes GUS ($\beta$-glucuronidase), can be used to test tissue specific regulatable expression from these promoters. Expression of GUS protein can be easily measured by fluorometric, spectrophotometric or histochemical assays (Jefferson, 1987a, 1987b, 1989).

The transformation method of the present invention is applicable to essentially all plants, including, but not limited to, fruit-bearing plants (e.g., tomatoes, raspberries, strawberries and melons), vegetables (e.g., cauliflower) and flowers (e.g., carnations). One such example is strawberries. The generation of pure transgenic strawberries, from two Pacific Northwest cultivars of strawberry, is described herein.

The present method is particularly useful in the transformation of woody species, that have historically had poor rates of transformation. When employing the transformation method of the present invention, transformation frequencies of woody species were greatly increased. One example of such a woody species is the red raspberry. The generation of transgenic raspberries, following the method of the present invention, is described below.

III. TRANSGENIC RASPBERRIES

Experiments performed in support of the present invention have yielded transgenic raspberry plants from a total of 218 independent transformation events (161 Meeker (MK), 4 Chilliwack (CH), 52 Canby (CY)). The transgenic plants have been established in soil for further evaluation of growth parameters an expression of the introduced traits.

Example 1 describes the growth response of Agrobacterium co-cultivated red raspberry explants when plated on media containing a selective agent. The cultivars were typically transformed with a binary vector in a disarmed A. tumefaciens strain. After co-cultivation, petioles and leaf explants were cultured on regeneration medium containing selective agent.

Figure 3A:
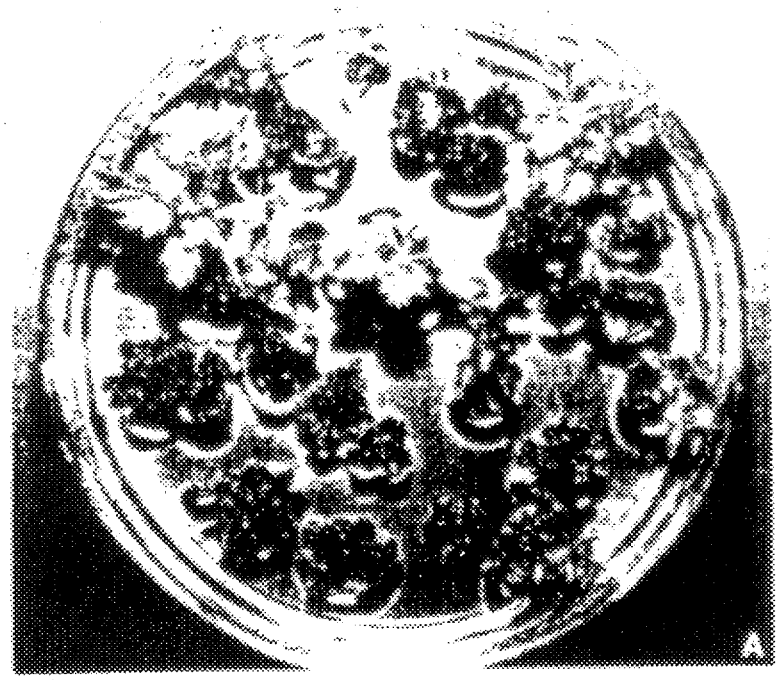
FIG. 3A represents petiole explants of red raspberry cv. Meeker with callus and shoot regenerants on regeneration edium with 30 mg/l hygromycin.

Cultivar Meeker explants showed de-differentiation of cut leaves in 3–4 weeks. After 6 weeks (end of second transfer period) about 24.0% of the leaf and 33.3% of the petiole explants underwent shoot regeneration. With subsequent transfers the number of petiole explants that underwent shoot regeneration increased (FIG. 3A; Table 1, Example 1).

The frequency of transformed cv. Meeker callus from both petiole and leaf explants was significantly higher than that of shoot regeneration and was capable of profuse growth in the presence of elevated levels of selective agent (relative to control explants). Typically, the percent recovery of transformed shoots was higher with petiole than with leaf explants.

Cultivar Chilliwack explants treated in similar fashion gave a transformation frequency of 0.9 and 0.7% from petiole and leaf explants, respectively, using the transformation method of the present invention (Example 1, Table 1).

Cultivar Canby was transformed with two binary vectors, pAG1552 and pAG1452, that each contain different selectable markers. Petiole and leaf explants after co-cultivation with pAG1552 were cultured on selection medium with geneticin. The explants co-cultivated with pAG1452 were cultured on regeneration medium with hygromycin for petiole and leaf explants.

Petioles proved to be more efficient explants than leaves in all the cultivars independent of whether the selection agent was hygromycin or geneticin. Transformation frequencies were obtained of 49.6% and 0.9% in the petiole and 15.9% and 0.7% in leaf explants for cultivars MK and CH respectively (Example 1). In cv. Canby the transformation rate ranged from 2.6–5.2% from petiole compared to 0.3–2.1% from leaf explants in different experiments.

In 3–4 weeks the cut edges of explants showed de-differentiation along with spontaneous shoot regeneration in some of the explants. Most of the shoot differentiation took place over a period of 4 months of culture on selection medium.

The responses of four independent experiments in cv. Canby are summarized in Table 1. As in the other two cultivars, the number of explants which gave transformed callus was significantly higher than the number of explants which gave rise to transformed shoots.

The hpt gene was found to be more efficient than nptII for recovering transformants. Experiments evaluating the different selection markers had shown that hygromycin and geneticin gave clear cut-off points compared to kanamycin in arresting the growth of raspberry tissue. Nevertheless, stable transgenic plants were obtained, at a frequency of 2.6–5.2% from petiole explants using the selection marker nptII gene. These results contradict the report of Graham, et al. (1990) that nptII gene is unsuitable as a selection marker gene for Rubus.

It was found that 50 mg/l kanamycin was inhibitory for organogenesis in Rubus and therefore, the transformants were raised in the absence of selection. It is possible that geneticin is a more effective antibiotic for Rubus than kanamycin although both antibiotics are aminoglycoside components that are detoxified by the neomycin phosphotransferase enzyme.

Frequency of shoot regeneration was higher with explants selected on medium with hygromycin while the frequency of transformed callus was higher with explants selected on medium with geneticin. Petiole explants gave higher rates of transformation both in terms of callus and shoot regeneration, irrespective of selection agent (Example 1, Table 1).

Transformed explants were periodically transferred to fresh media. From these samples, primary shoot regenerates were excised and individually cultured on shoot proliferation medium (Example 2) containing an appropriate selective agent. Upon transfer to such selective medium, the following four typical responses were observed:

(a) complete necrosis of the shoot (non-transformed escape);

(b) arrested shoot development with pale green leaves (non-transformed escape);

(c) vigorous growth of single shoot (putative transformant); and (d) multiple shoot proliferation (putative transformant).

Putative transformants were further analyzed for the presence of non-transformed regions by transfer of explants to selective medium. The process of explant isolation and reculture on selection medium was repeated only when isolated tissue explants were capable of growth on selection medium. This process, the iterative culture method, is continued under increasingly stringent selection levels. Pure transgenic plants are identified when all test explant tissue is determined to be resistant to the appropriate selective agent. Transgenic shoots were cultured on proliferation medium with selection for generating clonal plants of each transformation event (e.g., FIG. 3C).

The transformation method of the present invention employs a gradual increase in concentration of the selective agent, depending on tissue responses. Recovery of non-chimeral transgenics is valuable in plants, like raspberry, where the genetic constitution is maintained by vegetative means and recovery of pure transformants through seed segregation is not practical. However, since shoot meristems normally arise from more than one cell and also they need not arise from cells of clonal origin, the formation of chimeral plants is more of a rule than an exception in transformation experiments, particularly where plant regeneration occurs via organogenesis. This point was well-illustrated in recent reports on tobacco (Oono, et al., 1993; Schmulling and Schell, 1993), flax (Dong and McHughen, 1993a; Dong and McHughen, 1993b) and melon (Dong and McHughen, 1991).

As discussed above, putative transformants of raspberry were subjected to several iterations of tissue isolation and reculture on higher stringency selection for recovering uniformly-transformed plants. Shoots from each of the independent transformation events went through this rigorous screening procedure before they were considered as transformed. The transformation frequencies reported here were calculated only after such testing procedure.

Genomic DNA was isolated from putative transgenic plants and analyzed to confirm the presence of the transgenes and to characterize the structure of the integrated DNA (Example 3).

Figure 4A:
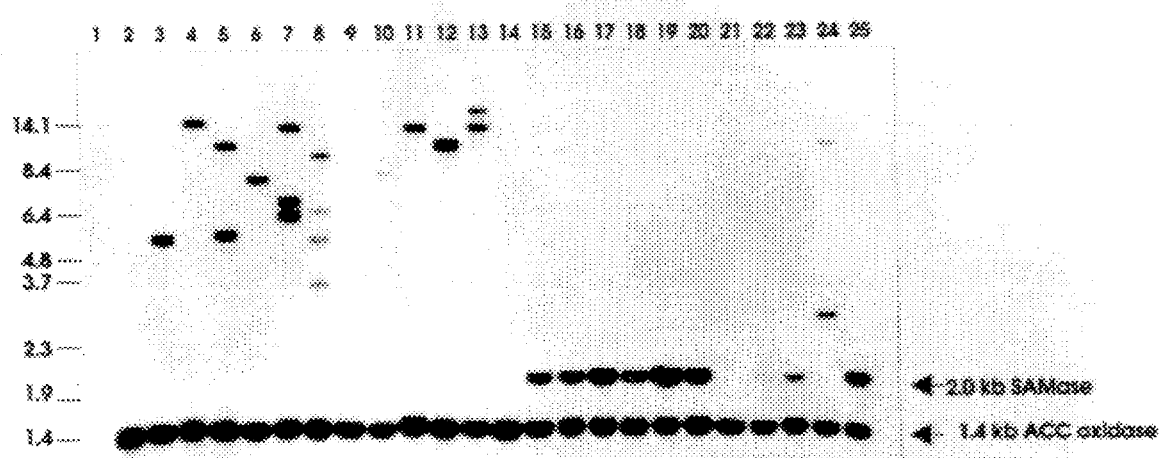
FIGS. 4A and 4B show Southern blots of DNA isolated from transgenic plants. In the figures, non-transformed Meeker (4A; lanes 2 and 14) and Canby (4B; lane 7) cvs. compared to DNA from independent transgenic lines in the same cultivars. DNAs were digested with either EcoRI alone (4A; lanes 2–13, 4B; lanes 1–6) or, in matching sequence, with both EcoRI and HindIII (4A; lanes 14–25, 4B; lanes 7–13). The blots were probed with a $^{32}$P-labeled probe consisting of either SAMase and a putative raspberry ACC oxidase gene (4A) or with SAMase alone (4B). The blot shown in 4B was also probed with the SAMase/ACC-oxidase probe which resulted in the expected 1.4 kb band appearing in each DNA track (not shown). Molecular weight markers in kb are shown along the left margins. Exposures were for 8 hours.
Figure 4B:
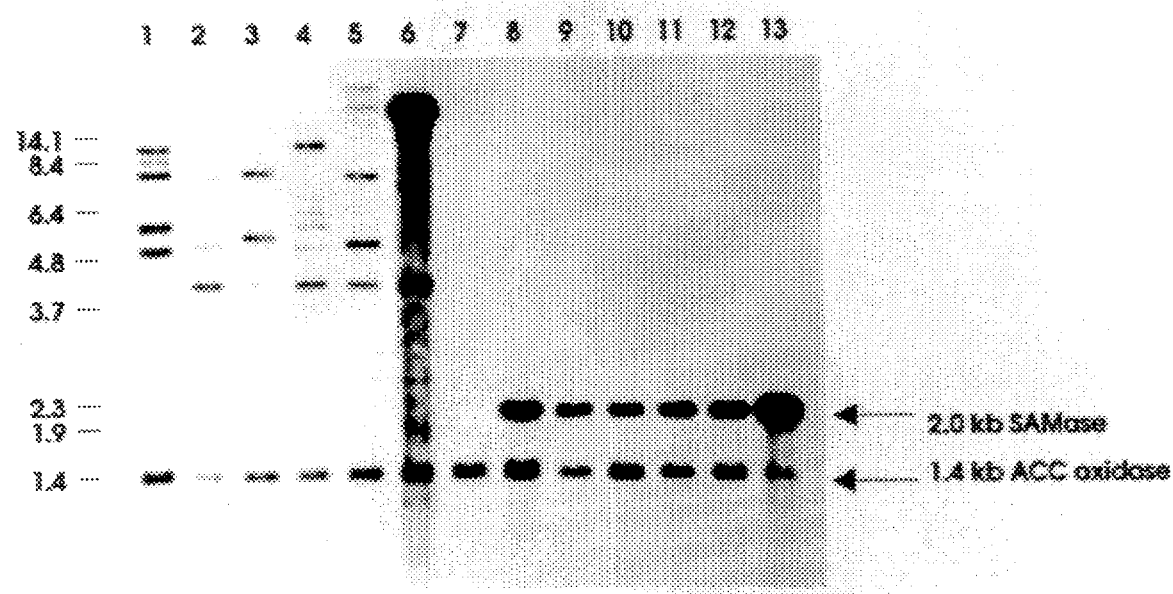

FIGS. 4A and 4B show the results of Southern analyses of genomic DNA isolated from transgenic plants obtained by the method of the present invention. In general, a variety of integration patterns were detected including single, double, and triple insertions and multiple insertions at a single site (Example 3). The majority of the transgenic plants investigated have intact single or double integration events.

Gene copy number for the Adometase gene, introduced by transformation, were also determined (FIGS. 4A and 4B). Gene copy number of the Adometase gene was typically determined relative to a putative raspberry ACC oxidase (ACCO) gene. A clone containing the putative raspberry ACCO gene was obtained by hybridization screening of raspberry genomic DNA library (Novagen, Madison, WI) using a probe derived from the tomato ACCO gene sequence (Hamilton, et al., 1991; Van der Straeten, et al., 1990).

A rather complex pattern of integration structures is seen in the results presented in FIG. 4B. It is interesting that these multiple integration patterns appear to be specific for the Canby cultivar and the nptII selectable marker gene.

Confirmed pure transgenic shoots (i.e., where (i) all explants are resistant to the appropriate selective agent, and (ii) the gene of interested was demonstrated to be present by Southern hybridization analysis) were transplanted directly to soil or cultured on rooting media then transplanted to soil in order to grow complete transgenic plants (Example 4).

Figure 3B:
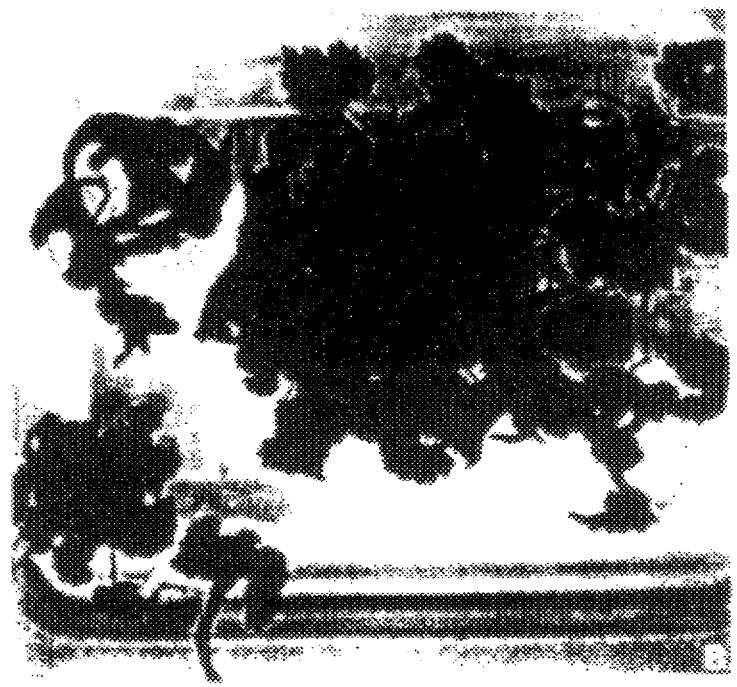
FIG. 3B illustrates shoot regenerants of red raspberry cv. Meeker on shoot proliferation medium with 15 mg/l hygromycin.
Figure 3C:
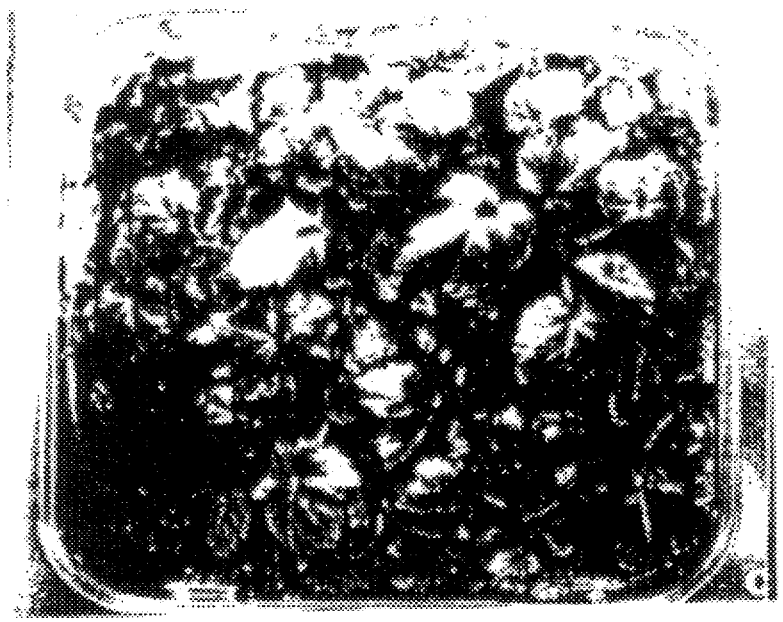
FIG. 3C shows transgenic clonal shoots of an event in cv. Canby.

Occasional abnormalities were observed among the transgenic plants (Example 5), however, only transgenic plants having normal appearance were transferred to soil. FIG. 3G shows exemplary transgenic plants established in greenhouse. These plants were indistinguishable from control non-tissue cultured plants.

The results presented above demonstrate the efficacious and reproducible generation of exemplary pure transgenic red raspberry plants.

IV. TRANSGENIC STRAWBERRIES

Experiments performed by the methods of the present invention have yielded about 500 transgenic strawberry plants from 250 independent transgenic events. The transgenic plants have been transferred to soil for further evaluation of growth parameters and expression of the introduced traits. A gene for the control of ethylene biosynthesis has been incorporated into strawberry (cultivar Totem) for the first time.

Examples 6 through 9 describe the general procedures utilized for co-cultivation, transformation, characterization, and rooting of two Pacific Northwest cultivars of strawberry, Tristar and Totem. As described in Example 10, cultivar Tristar was transformed with disarmed strains of Agrobacterium tumefaciens (A. tumefaciens), LBA4404 or EHA101, containing a binary vector with marker genes uidA and nptII.

Cultivar Totem was transformed with A. tumefaciens strains EHA101 or EHA105 harboring binary vectors with selectable marker genes nptII or hpt and with a gene for S-adenosylmethionine hydrolase (SAMase) for control of ethylene biosynthesis (Example 11). As shown in Table 2, the frequency of transgenic shoots in cultivar Totem ranged from 12.5% to 58.8% of the original treated explants when using plasmids containing the gene encoding SAMase.

Primary shoot regenerants obtained on selection medium were subjected to several iterations of tissue isolation and reculture on higher stringency selection medium to achieve recovery of uniformly transformed plantlets. Transgenic strawberry plants were confirmed by their ability to undergo rooting on medium with selection at 60 mg/l kanamycin or 10 mg/l hygromycin.

Greater than 95% of the transformation events from different experiments were capable of profuse rooting in the presence of selection agent, as described in greater detail in Example 11. Insertion of the SAMase gene and its integration into the strawberry genome were confirmed by Southern hybridization.

The results presented herein demonstrate the efficacious and reproducible generation of exemplary pure transgenic strawberry plants.

V. UTILITY

A. THE TRANSFORMATION METHOD OF THE PRESENT INVENTION

The transformation frequency obtained by the method of the present invention is the highest that has been obtained for Rubus species or for any other woody fruit crops. It is also to be noted that the regenerants and callus from one explant were treated as one event although it is possible to have more than one transformation event per explant. This implies that the actual transformation efficiency is even higher than the figures reported herein. The more conservative figure was used to avoid possible errors in separating independent events.

The transformation method of the present invention, provides a high efficiency transformation system for plants in general and also means to generate pure (or non-chimeric) transgenic plants. The ability to recover a large number of transgenic events is important for the purpose of field testing of transgenic plants, in view of the typical development of somaclonal variants and variations in transgene expression due to gene copy number and positional effect.

The transformation method of the present invention was also used to incorporate, for the first time, a gene controlling ethylene biosynthesis into the strawberry cultivar Totem. Transformation efficiency ranged from 12% to nearly 60%.

The method of the present invention provides a high rate of transformation frequency and generation of pure transgenic plants. Examples are described herein for strawberry and red raspberry. Red raspberry (Rubus idaeus L.) has historically been recalcitrant to molecular genetic manipulations.

B. TRANSGENIC FRUIT: RED RASPBERRIES AND STRAWBERRIES

Increased fruit firmness is a component of reduced susceptibility to fruit rot, a major factor in the extension of fresh market shelf life (Daubeny and Anderson, 1993). Controlling the metabolic processes which cause ripening has the potential to improve shelf life, extend the harvest season and the market area for highly perishable or easily damaged fruits.

Transgenic tomatoes with increased firmness and pronounced delay in ripening were obtained by incorporating a gene for S-adenosylmethionine hydrolase (see above). Adometase catalyses the conversion of S-adenosylmethionine (SAM) to methylthioadenosine (MTA) and homoserine which can reenter the methionine recycling pathway (FIG. 1). SAM is therefore not available for the synthesis of aminocyclopropane-1-carboxylic acid (ACC), the metabolic precursor for ethylene synthesis. Transgenic tomatoes with the Adometase gene, which are now undergoing field trials, showed a greatly-reduced ability to synthesize ethylene and significantly increase post-harvest shelf-life.

Ethylene is reported to play a major role in the ripening and abscission of raspberry fruit (Sexton, et al., 1993). Perkins-Veazie, et al. (1992) observed that a dramatic increase of ethylene production during the fruit ripening of raspberry. The Adometase gene has now been incorporated into red raspberry cultivars in order to test the efficacy of the gene to reduce softening and increase the shelf-life of berries.

Although strawberry is not considered a typical climacteric fruit (Kader, 1991), there is evidence that indicates that the removal of ethylene may also play a role in reducing spoilage of fresh berries such as strawberries. Exogenous application of ACC (the immediate metabolic precursor to ethylene), to 'Earlyglow' strawberry at preclimacteric and climacteric stages induced higher ethylene production while AVG (ethylene antagonist) application inhibited the biosynthesis of ethylene (Basiouny, 1989).

Treatment of strawberry cv. Chandler with ethylene absorbent gave increased firmness combined with reduced fungal attack (De la Plaza and Merodia, 1989). The SAMase gene has also been introduced into a Pacific Northwest variety of strawberry, cultivar Totem, to examine the efficacy of the gene to reduce softening and increase the post-harvest life of strawberries.

Transgenic fruit, such as transgenic raspberries and strawberries can also be generated containing other functional genes that affect fruit and plant characteristics, for example, the following:

(i) increased sugar content of fruit;

(ii) increased fungal and/or viral resistance of plants and/or fruit; and (iii) reduced ethylene biosynthesis.

The following examples illustrate, but in no way are intended to limit the present invention.

MATERIALS AND METHODS

A. EXPLANT SOURCE

Leaves, meristematic tissue and petioles were excised from proliferating shoot cultures maintained on modified MS medium (Murashige and Skoog, 1962) supplemented with 1 mg/l benzylaminopurine (BA) and gelled with 0.2% phytagel. Typically, the following tissue sources were not used for explant isolation: leaves and petioles from the 2-3 nodes close to the shoot tip, and leaves of greater than 10 mm in size.

Petioles were cut into 4-6 mm segments. Leaf blades 4-5 mm in length were used as whole explants or they were cut into transverse halves when blades were greater than 6 mm in size.

Leaf explants were cultured with the adaxial surface in contact with the medium.

Meristematic tissue was obtained by excision of 10-12 mm sections of the actively proliferating base of 3-4 week old strawberry plants maintained in vitro on propagation medium. These sections typically contained the apical meristem region from several shoot buds.

B. BACTERIAL STRAIN AND BINARY VECTORS

Agrobacterium tumefaciens strain EHA105 contained the disarmed super-virulent plasmid pTiBo452 in the C58 chromosomal background (Hood, et al., 1993).

The plasmid vectors containing the S-adenosylmethionine hydrolase (Adometase or SAMase) gene (were constructed using the backbone of pGPTV binary vectors (Becker, et al., 1992) where the marker genes had been divergently organized for efficient expression and could be easily removed or replaced.

The AdoMetase gene was identified on an AluI-HaeIII restriction fragment from purified T3 DNA (Hughes, et al., 1987a). Bacteriophage T3 is available under ATCC No. 11303-B3 (American Type Culture Collection, 12301 Parklawn Dr., Rockville MD 20852). The DNA fragment was first cloned into the bacteriophage M13 MP8 vector (Pharmacia LKB Biotechnology, Inc., Pistcataway, N.J.). A MaeIII to BamHI fragment was subcloned into the pUC19 plasmid vector (Pharmacia) to produce pUC19-AdoMetase. This vector was transformed into $E.\ coli$ and used as a source of Adometase DNA.

Figure 2A:
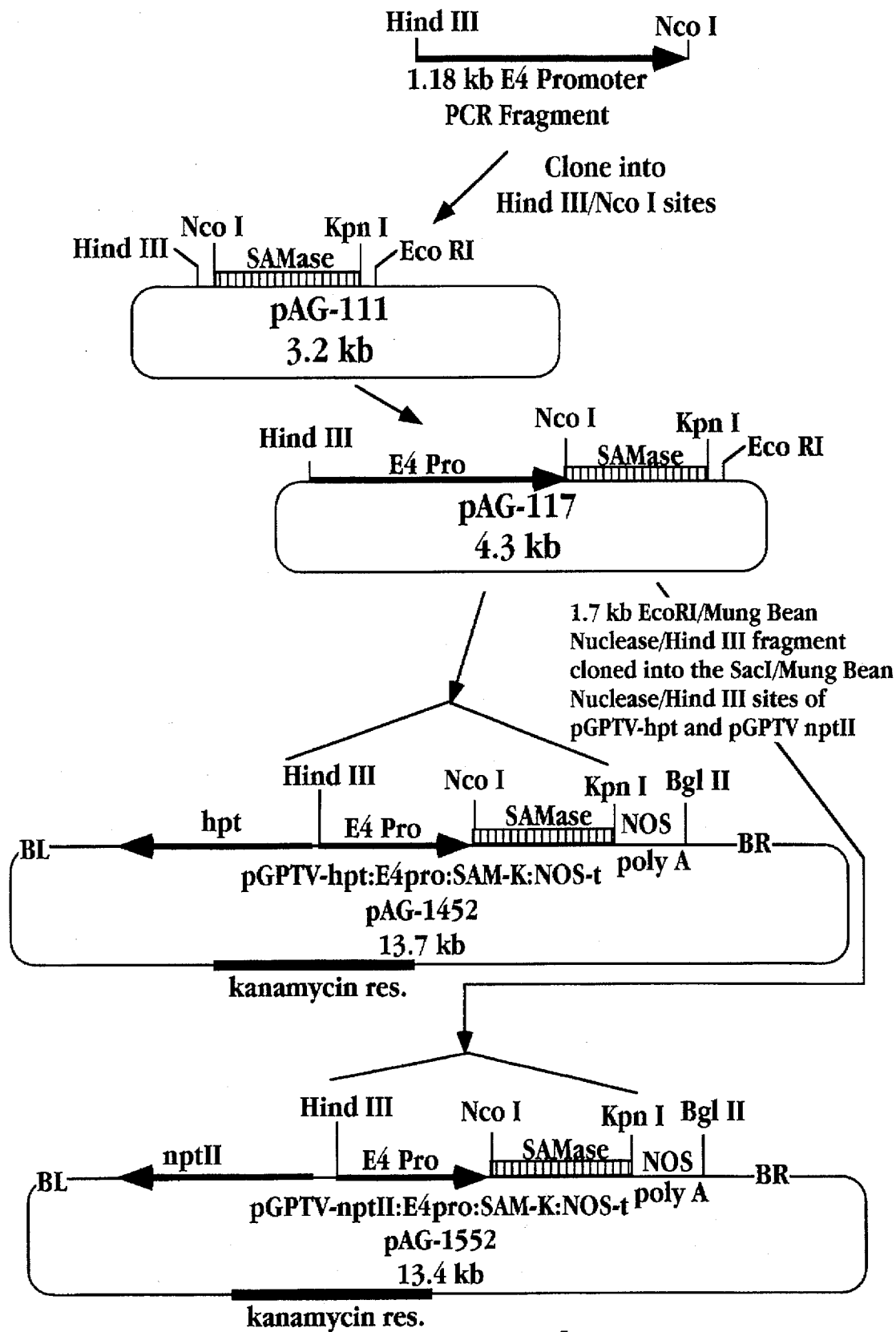
FIG. 2A shows a flow chart outlining the construction of the Agrobacterium tumefaciens binary vectors used in th resent study (pAG-1452 and pAG-1552).

The constructions of vectors pAG-1452 and pAG-1552 are shown schematically in FIG. 2A. A 1.18 kb tomato E4 promoter containing fragment was generated using E4-specific polymerase chain reaction primers (Cordes, et al., 1989) containing HindIII and NcoI cleavage sites. The promoter sequences were cloned adjacent the 5' end of the Adometase gene (FIG. 2A, pAG-117). The sequence of the E4 promoter/Adometase gene construct is presented as SEQ ID NO:6.

A 1.7 kb fragment, containing the E4 promoter and Adometase coding sequences, was obtained from pAG-117 by EcoRI/Mung Bean nuclease/HindIII digestion. This fragment was cloned into the SacI/Mung Bean Nuclease/HindIII sites of the vectors pGPTV-hpt and pGPTV-nptII (FIG. 2A).

Figure 2B:
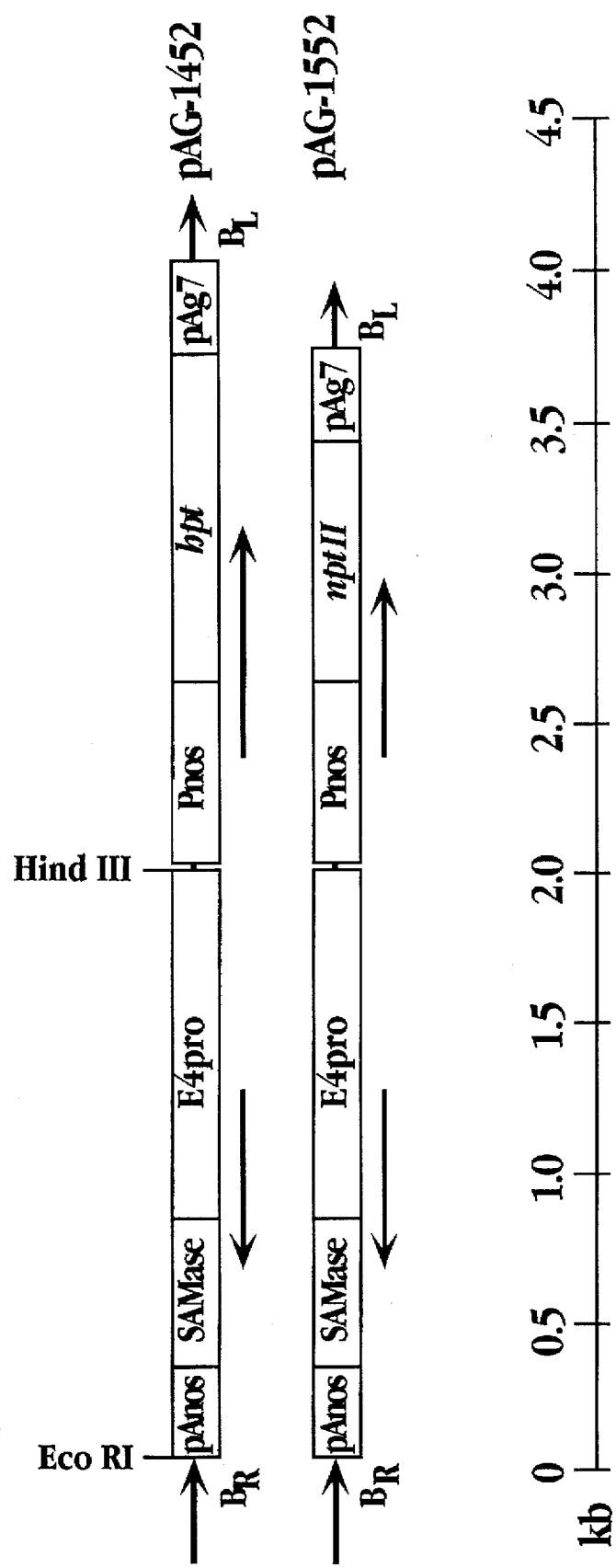
FIG. 2B shows restriction maps of these vectors. The EcoRI and HindIII sites shown in pAG1452 are present at the same location in pAG1552. The agrobacterium Ti right and left borders are abbreviated $B_R$ and $B_L$, respetively.

The binary vector, pAG1452 had the hpt gene for resistance to the antibiotic hygromycin under the nos promoter located near the left border and the SAMase gene driven by the tomato E4 promoter (Gamborg, et al., 1968) located near the right border (FIGS. 2A and 2B).

The binary vector pAG1552 differed from pAG1452 by having the nptII marker gene in place of the hpt gene (FIGS. 2A and 2B).

C. CO-CULTIVATION OF EXPLANTS WITH AGROBACTERIUM

A freshly-grown single colony of Agrobacterium was inoculated into 30 ml of MG/L (Garfinkel and Nester, 1980) liquid medium supplemented with 50 AM acetosyringone, pH. 5.6, was grown on a shaker at 200 rpm for overnight (16-18 hours). The bacterial suspension had an average count of 0.5-0.6 $\times 1^{09}$ cells/ml at the start time of co-cultivation with plant tissues.

The petioles and leaf explants soon after excision were soaked in Agrobacterium suspension. After 30-60 minutes, these were transferred to flasks containing liquid medium of composition-modified MS (Murashige and Skoog, 1962) salts, B5 (Gamborg, et al., 1968) vitamins, 2 mg/l glycine, sucrose 3%, 1-4 mg/l BA, 0.2 mg/l IAA and 50 µM acetosyringone, pH 5.6, and kept on shaker at 100 rpm. The density of explants is about 100-120 segments in about 30 ml of medium in 125 ml flasks.

The next day, the medium was decanted and replaced with fresh liquid medium of the same composition and kept on the shaker. After 2 days of co-cultivation, the explants were rinsed with liquid medium without acetosyringone, blotted and plated on regeneration medium containing a selection agent (e.g., kanamycin, G418 - geneticin, or hygromycin).

At the end of co-cultivation period if the suspensions turned visibly cloudy with Agrobacterium growth, the explants were incubated with liquid medium, supplemented with 500-1000 mg/l cefotaxime for one hour on the shaker before blotting and plating on screening medium.

D. TISSUE CULTURE MEDIUM AND GROWTH CONDITIONS

The shoot regeneration/proliferation medium consisted of MS (Murashige and Skoog, 1962) salts, B5 (Gamborg, et al., 1968) vitamins, 2 mg/l glycine sucrose 3%, supplemented with IBA 0.1 mg/l, 0.1-1.0 mg/l TDZ and 10 mg/l silver nitrate.

For cultivar Meeker, 3% sucrose was replaced by 3% D-glucose as the carbon source. The pH of the medium was adjusted to 5.8 before gelling with 0.2-0.25% phytagel.

The culture medium was autoclaved at 120° C. at 1.1 kg.cm². The antibiotics and silver nitrate which were filter sterilized and added as the media cooled. Depending on the plasmid strain the regeneration medium contained antibiotics carbenicillin (500 mg/i) and geneticin (3-25 mg/i) or hygromycin (10-30 mg/i) for screening of transformed shoots.

Cultures were kept at 25° C with 16-hour photo—period provided by white fluorescent light at an average intensity of 50 µmol m$^{-2}$ s$_{-1}$. Observations were recorded every 3-4 weeks and cultures were transferred to fresh medium of the same composition with appropriate changes in the level of antibiotics.

Soon after co-cultivation the explants received the lowest level of selection (threshold concentration of the selection agent). The concentration for the initial selection was typically a media concentration of the selective agent that was able to essentially prevent the growth of the corresponding non-transformed cultivar (e.g., non-transformed Meeker as a control for transformed Meeker).

As the explants underwent proliferation in culture, the selection level was gradually increased based on the rate of dedifferentiated tissue on the explant. The selection level was elevated to a maximum of 25 mg/l of geneticin or 30 mg/l hygromycin in the case of explants with prolific callus growth.

Putatively transformed red shoot regenerants were isolated and cultured on shoot proliferation medium with selection at 14–20 mg/l of geneticin or hygromycin. Rooting medium for transgenic shoots contained half MS (Murashige and Skoog, 1962) salts, B5 vitamins (Gamborg, et al., 1968), 3% sucrose (or D-glucose for cv. Meeker), 0.05 mg/l IBA, 300 mg/l carbenicillin and 10 mg/l hygromycin or geneticin.

Leaf, petiole and nodal explants were cultured in petri plates with 40 ml of regeneration/proliferation medium. Typically, there were 20 petiole segments and 10 leaf segments per plate. Shoot explants (6–9) for multiplication/rooting were cultured on phytatrays with 120 ml of the proliferation or rooting medium.

E. TREATMENT OF PRIMARY SHOOT REGENERANTS AND RECOVERY OF TRANSGENIC CLONES

Shoot regenerants were isolated and cultured on shoot proliferation medium containing 15–20 mg/l geneticin or hygromycin. Leaves, petioles and nodal segments were isolated from shoots which withstood selection, and cultured on regeneration or proliferation medium with 20 mg/l geneticin or hygromycin. This iterative process of reculture of excised tissues from regenerants was continued until no part of the shoots necrosed or bleached under selection pressure ("bleaching" is loss of significant amounts of chlorophyll).

Shoots were considered as fully transformed (i.e., non-chimeric or pure) only after they passed the above criteria. Such shoots were multiplied on proliferation medium for generating clonal plants derived from different transformation events. Tissue samples from such plants were used for molecular confirmation of transformation events.

F. TRANSFORMATION EFFICIENCY

Frequency of transformation was defined as "the number of explants that gave antibiotic resistant callus and/or shoot regenerants" relative to "the total number of co-cultivated explants." Transformation frequency was expressed in percentage points.

G. ESTABLISHMENT OF TRANSGENIC SHOOTS/PLANTS IN THE GREEN HOUSE

Individual shoots were isolated from profusely proliferating shoots, growing on selection medium, for root induction or were transferred directly to soil.

For direct transfer to soil, the shoot base was dusted with rooting mix (Hormex powder #3) before placing in potting mix. Phytatrays with rooted plants were kept in the greenhouse with loosened lids for 2–4 days, followed by transfer to soil after rinsing off the media with water.

H. GENOMIC DNA HYBRIDIZATION ANALYSIS

Genomic DNA was isolated from leaf tissue of transgenic and non-transformed control plants following the method of Dellaporta, et al. (1983). The DNA was digested with either EcoRI or EcoRI and HindIII, the restriction digestion fragments electrophoretically separated, transferred to a nylon membrane (Oncor, Gaithersburg, MD), hybridized with $^{32}$p radiolabeled probes and autoradiographed using standard procedures (Sambrook, et al., 1989; Ausubel, et al.).

The hybridization probes used were a 550 bp fragment containing the SAMase gene or a 1050 bp fragment containing the genes for SAMase and a putative raspberry aminocyclopropane-1-carboxylic acid oxidase (ACCO) gene (obtained by hybridization of a tomato ACCO gene-specific probe (Hamilton, et al., 1991; Van der Straeten, et al., 1990) to a library of raspberry genomic DNA (Novagen)). Transgene copy number was estimated by comparing the ACCO and SAMase band intensities using a high-resolution flat bed scanner and the "NIH-Image" image analysis program on an Apple MacIntosh Computer.

EXAMPLE 1

RESPONSE OF CO-CULTIVATED RASPBERRY EXPLANTS ON SELECTION MEDIUM

A. cv. MEEKER

Cultivar Meeker was transformed with the binary vector pAG1452 in the disarmed A. tumefaciens strain EHA105. After co-cultivation, petioles and leaf explants were cultured on regeneration medium with 10 mg/l hygromycin. In 3–4 weeks de-differentiation of cut leaves was observed. At the end of the second transfer period (6 weeks), about 24.0% of the leaf and 33.3% of the petiole explants underwent shoot regeneration.

The number of petiole explants undergoing shoot regeneration (FIG. 3A) increased with subsequent transfers. The petiole explants gave 49.6% shoot regeneration at the end of 4 months of culture on selection medium (Table 1).

TABLE 1

FREQUENCY OF TRANSFORMATION OBTAINED IN RED RASPBERRY CVS. MEEKER, CHILLIWACK, AND CANBY

| Cultivar | Expt ID | Plasmid | Explant | # Initial Explants | Transformation Frequency % Callus | Transformation Frequency % Shoot Regn | No. of Events in Soil |
|---|---|---|---|---|---|---|---|
| Meeker | RT18 | pAG1452 | Petiole | 244 | 74.1 | 49.6 | 88 |
|  |  | pAG1452 | Leaf | 675 | 31.3 | 15.9 | 73 |
| Chilliwack | RT18 | pAG1452 | Petiole* | 214 | 37.0 | 0.9 | 2 |
|  |  | pAG1452 | Leaf* | 430 | 14.4 | 0.7 | 2 |
| Canby | RT24 | pAG1552 | Petiole | 467 | 91.4 | 2.6 | 10 |
|  |  | pAG1552 | Leaf | 314 | 0.3 | 0.3 | 1 |
| Canby | RT25 | pAG1552 | Petiole | 190 | 95.8 | 3.7 | 4 |
|  |  | pAG1552 | Leaf | 223 | 9.4 | 0 | 0 |
| Canby | RT28 | pAG1552 | Petiole | 308 | 66.9 | 5.2 | 5 |
|  |  | pAG1552 | Leaf | 322 | 43.5 | 3.1 | 8 |
| Canby | RT27 | pAG1452 | Petiole | 308 | 51.6 | 8.1 | 19 |
|  |  | pAG1452 | Leaf | 288 | 30.6 | 2.4 | 6 |

Note: Culture period 120 to 125 days, ~50% explants lost due to contamination.

The shoot regeneration frequency of leaf explants decreased to 15.9% at the end of 4 months culture since many of the early regenerants underwent complete necrosis (FIG. 3B) after transfer to proliferation medium with hygromycin. Frequency of transformed callus from both petiole and leaf explants was significantly higher than that of shoot regeneration and was capable of profuse growth in the presence of 30 mg/l hygromycin.

Control leaf and petiole explants did not withstand even 10 mg/l hygromycin and were completely necrosed by the second culture period. The percent recovery of transformed shoots was higher with petiole than with leaf explants.

B. cv. CHILLIWACK

As shown in Table 1, cv. Chilliwack treated with A. tumefaciens strain EHA 105 containing the binary vector pAG1452, gave a transformation frequency of 0.9 and 0.7% from petiole and leaf explants respectively. Initially 25% of the petiole and 9.8% leaf explants underwent shoot regeneration during 4–6 weeks culture on regeneration medium with selection at 10 mg/l hygromycin. But many of these initial shoot regenerants necrosed upon excision and culture on proliferation medium with the addition of selective agent. In addition, many of the leaf explants appear to have been lost due to hypersensitivity to Agrobacterium during the co-cultivation period.

C. cv. CANBY

Cultivar Canby was transformed with both binary vectors, pAG1552 and pAG1452. Petiole and leaf explants after co-cultivation with pAG1552 were cultured on selection medium with geneticin 5 and 10 mg/l geneticin, respectively. The explants co-cultivated with pAG1452 were cultured on regeneration medium with 10 and 20 mg/l hygromycin for petiole and leaf explants, respectively.

In 3–4 weeks the cut edges of explants showed de-differentiation along with spontaneous shoot regeneration in some of the explants. Most of the shoot differentiation took place over a period of 4 months of culture on selection medium.

The responses of four independent experiments in cv. Canby, three with plasmid pAG1552 and one with pAG1452 are summarized in Table 1. As in the other two cultivars, the number of explants which gave transformed callus was significantly higher than the number of explants which gave rise to transformed shoots. The transformed callus grew uninhibited at 25 mg/l geneticin or 30 mg/l hygromycin depending on the transgene nptII or hpt while growth of control non-transformed tissues was completely inhibited at much lower concentrations, 5–10 mg/l.

Frequency of shoot regeneration was higher with explants selected on medium with hygromycin while the frequency of transformed callus was higher with explants selected on medium with geneticin. Petiole explants gave higher rates of transformation both in terms of callus and shoot regeneration, irrespective of selection agent.

EXAMPLE 2

TREATMENT OF PRIMARY RASPBERRY SHOOT REGENERANTS AND RECOVERY OF TRANSGENIC CLONES

During the periodic transfer of leaf and petiole explants to fresh medium, the differentiated shoots, about 10–15 mm in size, were excised and individually cultured on shoot proliferation medium with 15–20 mg/l geneticin/hygromycin depending on the strain pAG1452 or pAG1552 used in the experiment.

Mainly four types of responses were observed: (a) complete necrosis of the shoot; (b) arrested shoot development with pale green leaves; (c) vigorous growth of single shoot; and (d) multiple shoot proliferation. Among these, the first two categories were considered as non-transformed escapes or with very few transformed cell population and discarded. Vigorously-growing single-shoot and multiple-shoots were considered putative transformants and used for further analysis to check whether the whole shoot was uniformly transformed.

Leaves, petioles, and nodal explants of the primary regenerants were excised and cultured on regeneration/proliferation medium with 20 mg/l of the selection agent geneticin/hygromycin. The majority of the explants underwent callusing and shoot regeneration, or bud growth in the case of nodal segments, while some of the explants necrosed and responded like corresponding control, non-transformed tissues on selection.

When the presence of such non-transformed regions were identified in the putative transformants, the process of explant isolation and reculture on selection medium was repeated only when isolated tissue explants were capable of growth on selection medium. Transgenic shoots were then cultured on proliferation medium with selection for generating clonal plants of each event (FIG. 3C).

EXAMPLE 3

GENOMIC DNA HYBRIDIZATION ANALYSIS OF TRANSGENIC RASPBERRY PLANTS

DNA isolated from putative transgenic plants were subjected to DNA hybridization (Southern) analysis to confirm the presence of the transgenes and to characterize the structure of the integrated DNA.

Plant genomic DNA was isolated and evaluated as described above. The DNA was digested with EcoRI alone or in conjunction with HindIII. EcoRI cleaves the region between the borders of the binary vector once and therefore produces junction fragments that can be recognized by hybridization of cleaved DNA with an Adometase probe (FIG. 2B). Junction fragments can provide information on the transgene copy number and the number of independent integration events.

The EcoRI/HindIII double digest produces a single fragment internal to the T-DNA borders that can be also be detected using an Adometase hybridization probe.

FIGS. 4A and 4B show the results of Southern analyses of genomic DNA isolated from transgenic cv. Meeker with pAG-1452, and cv. Canby with pAG-1552, respectively. In general, a variety of integration patterns were detected including single, double, and triple insertions and multiple insertions at a single site.

FIG. 4A, lanes 3 to 13, show the junction fragments from eleven transgenic events in cv. Meeker. Most are single integration events with one double (lane 5) and one triple (lane 7) event. Lane 8 is aberrant due to the unusually faint bands and the observation that one band is smaller than the predicted 4.2 kb EcoRI to left border fragment size of pAG-1452 (see FIG. 2B). Lanes 9 and 10 contain faint, single copy bands.

In FIG. 4B, the EcoRI digested DNA produced bands that seem to fall into two intensity categories suggesting a complex integration structure.

Estimates of the SAMase gene copy number were also made using a hybridization probe consisting of both the SAMase gene and a putative raspberry ethylene-forming enzyme gene or ACC oxidase (ACCO) which has one allele. The ACCO probe produces a band intensity equivalent to two copies of the gene. It also serves to confirm that the DNA has been completely digested by EcoRI and provides a measure of the relative amounts of DNA in each lane.

Because the ACCO and SAMase genes are on a single plasmid from which the double hybridization probe is made, the intensity differences between the EcoRI/HindIII SAMase bands and the EFE bands can be compared and were used to quantitate the SAMase gene copy number.

In FIG. 4A there is good agreement between the number of integrations predicted by the junction fragment analysis and the intensity of the EcoRI/HindIII SAMase bands.

In FIG. 4B the copy number estimation places limitations on the possible integration structures predicted by the EcoRI pattern. One line had multiple integrations (see FIG. 4B, lanes 6 and 13) estimated at greater than 20 copies of the SAMase gene.

EXAMPLE 4

ROOTING AND TRANSPLANTATION OF TRANSGENIc RASPBERRY SHOOTS

Figure 3D:
FIG. 3D shows transgenic plant of cv. Meeker rooted on medium with 10 mg/l hygromycin, ready for outplanting to oil.

Individual shoots isolated from multiple shoot complex were cultured on rooting medium with selection at 10 mg/l geneticin or hygromycin (FIG. 3D). All the rooted shoots were successfully transplanted to soil. When shoots were directly transplanted to soil from proliferation medium, the survival rate was typically 60-70%.

EXAMPLE 5

OCCASIONAL ABNORMALITIES AMONG RASPBERRY TRANSGENICS

Figure 3E:
FIG. 3E shows stunted shoots from transformed regenerants of cv. Canby.

In cultivar Canby (RT24 experiment, Table 1) one of the events gave bristle type shoots on regeneration medium. These shoots were stunted in appearance and had limited expansion of leaf lamina (FIG. 3E).

Figure 3F:
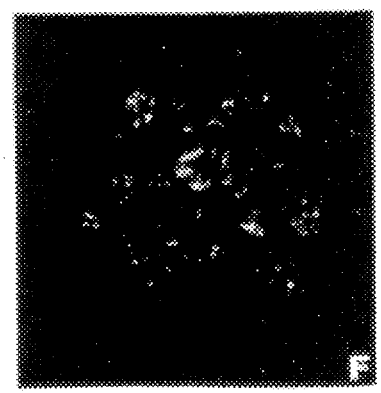
FIG. 3 shows bud differentiation on leaf lamina of cv. Meeker.
FIG. 3G shows transgenic plants of cv. Meeker established in greenhouse.
Figure 3G:
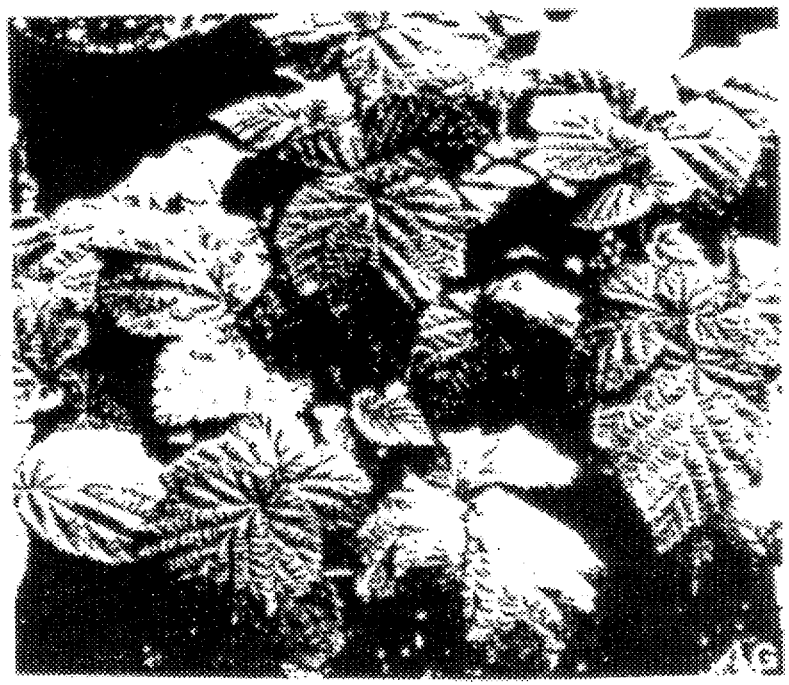

In cv. Meeker an interesting kind of shoot regeneration was observed occasionally on leaves of some of the transgenic shoots. Shoot buds arose from all over the adaxial surface of leaves still attached to the shoots growing in proliferation medium with selection. If these leaves were detached and placed on the same shoot proliferation medium, the shoot buds developed into shoots (FIG. 3F). This phenomenon was not observed in the control non-transformed proliferation cultures while stunted and bristle type shoots were occasionally observed among the control regenerants.

Only transgenic plants having normal appearance were transferred to soil. FIG. 3G shows transgenic plants established in greenhouse. These plants were indistinguishable from control non-tissue cultured plants.

EXAMPLE 6

EXPLANTS AND CULTURE CONDITIONS FOR STRAWBERRY CULTIVARS

The explants source was provided by three to four week old cultures of the strawberry cultivars, Tristar and Totem, maintained in vitro on propagation medium. The propagation medium contained the following: basal medium (Murashige and Skoog, 1962), 1 mg/l indoleacetic acid (IAA), 1 mg/l benzylaminopurine (BA), and 0.01 mg/l gibberellic acid (GA); maintained at pH 5.8, and gelled with 0.8% agar (Sigma A1296).

Meristematic sections (10–12 mm) of the actively proliferating base of cultivar Tristar explants (containing several shoot buds) were co-cultivated with A. tumefaciens. Co-cultivation of cultivar Totem explants with A. tumefaciens was carried out using either leaf or petiole tissues from the explant, or whole young shoots (5–7 mm in length), segmented into 2–3 mm pieces. Cultivar Totem petioles were cut into 4–6 mm sized sections prior to co-cultivation. Folded young leaves explants (4–6 mm in length) were cut longitudinally and cultured with the adaxial surface in contact with the propagation medium.

Leaf, petiole and shoot base explants were cultured in petri plates (Nalgene, 100×25mm) containing 40 ml medium. Each petri plate contained 20–25 explant segments. Shoots for proliferation or rooting were cultured in "PHYTATRAYS II" (Sigma) containing 120 ml medium and from 9–10 shoots per tray.

All media components were autoclaved at 120° C. at 1.1 kg cm$^{-2}$, with the exception of the antibiotics, acetosyringone and silver nitrate, which were filter sterilized prior to addition to the medium. All experimental and stock cultures were maintained at 25° C. with 16 hour photoperiods provided by cool white fluorescent lamps at an average intensity of about 15–20 umolm$^{-2}$ s$^{-1}$. Observations were recorded every 3–4 weeks followed by transfer to fresh medium.

EXAMPLE 7

TRANSFORMATION OF STRAWBERRY EXPLANTS

A. PREPARATION OF BACTERIAL SUSPENSIONS

A freshly grown single colony of A. tumefaciens (LBA4404, EHA101 or EHA105) was inoculated into 30 ml of MG/L (Garfinkel and Nester, 1980) liquid medium supplemented with 50 AM acetosyringone, pH 5.6, and grown on a shaker overnight (16–18 hours, 200 rpm). The resulting bacterial suspension had an average count of 0.5–0.6×10$^9$ cells/ml at the start time of co-cultivation with plant tissues.

B. BACTERIAL STRAINS AND BINARY VECTORS

Disarmed A. *tumefaciens strains*, LBA4404, EHA101 and EHA105, were used for strawberry transformation (Hood, et al., 1994).

Figure 5:
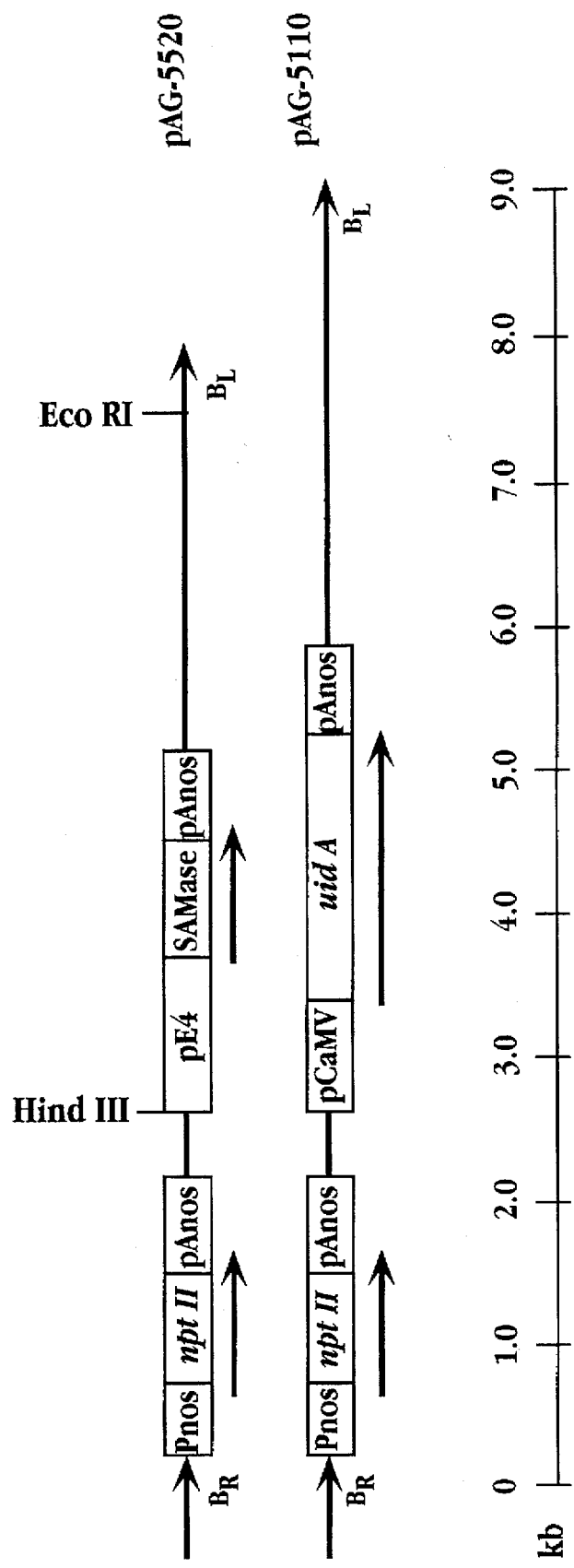
FIG. 5 shows restriction maps of A. tumefaciens binary vectors used as transformants. The EcoRI and HindIII sites indicated are present in the same location for both vectors pAG5520 and pAG5110. The agrobacterium right and left borders are abbreviated $B_R$ and $B_L$, respectively.

The binary vectors, pAG5110 and pAG5520, were derived from pGA482 (An et al., 1985). The binary vector, pAG5110, contained DNA sequences encoding both the uidA gene under the transcriptional control of the CaMV35S promoter, and the nptII gene, under the transcriptional control of the nopaline synthase (nos) promoter. The plasmid vector, pAG5520, contained the SAMase gene with the tomato fruit specific E4 promoter (Cordes et al., 1989) and the nptII gene, under the transcriptional control of the nos promoter (FIG. 5).

The binary vectors, pAG1552 and pAG1452, were constructed using the backbone of the pGPTV binary vector (Becker et al., 1992). The vector constructs contained the SAMase gene driven by the E4 promoter (Cordes et al., 1989) located near the right border and the marker gene nptII (pAG1552) or hpt (pAG1452) under the nos promoter located near the left border (FIG. 2B).

C. CO-CULTIVATION WITH *A. TUMEFACIENS*.

Shortly following excision, isolated explants, as described in Example 6, were soaked in A. tumefaciens suspension.

After 60–90 minutes, the explants were blotted on sterile filter paper and transferred to flasks containing liquid culture medium of MS basal salts (Murashige and Skoog, 1962), B5 (Gamborg et al., 1968) vitamins, 3% sucrose, 2 mg/l BA, 0.5 mg/l IAA, 50–100 µM acetosyringone, pH 5.6, gelled with 0.25% "PHYTAGEL".

After 2 days of co-cultivation, the explants were rinsed with fresh liquid medium lacking acetosyringone, and incubated in flasks containing liquid medium supplemented with 500–1000 mg/l cefotaxime. The explant-containing flasks were placed on a shaker for 1 hour (100 rpm) before blotting the explants and plating on screening medium containing a selection agent.

D. SCREENING MEDIUM FOR SELECTION OF TRANSFORMANTS

The screening medium consisted of MS (Murashige and Skoog, 1962) salts, B5 (Gamborg et al., 1968) vitamins, 3% sucrose, 0.1–0.2 mg/l IBA, 5–10 mg/l BA, 500 mg/l carbenicillin (Gemini Bio-Products, Inc., Calabasas, Calif.) and one of the following selection agents: kanamycin (Sigma, St. Louis, MO), geneticin (Gibco, Gaithersburg, MD) or hygromycin (Calbiochem, San Diego, Calif.).

The initial selection levels of antibiotic were determined from the tolerance of non-transformed control tissue to the antibiotic selection agents. The concentration for the initial selection was typically a media concentration of the selection agent that was able to essentially prevent the growth of the corresponding non-transformed cultivar.

Figure 13:
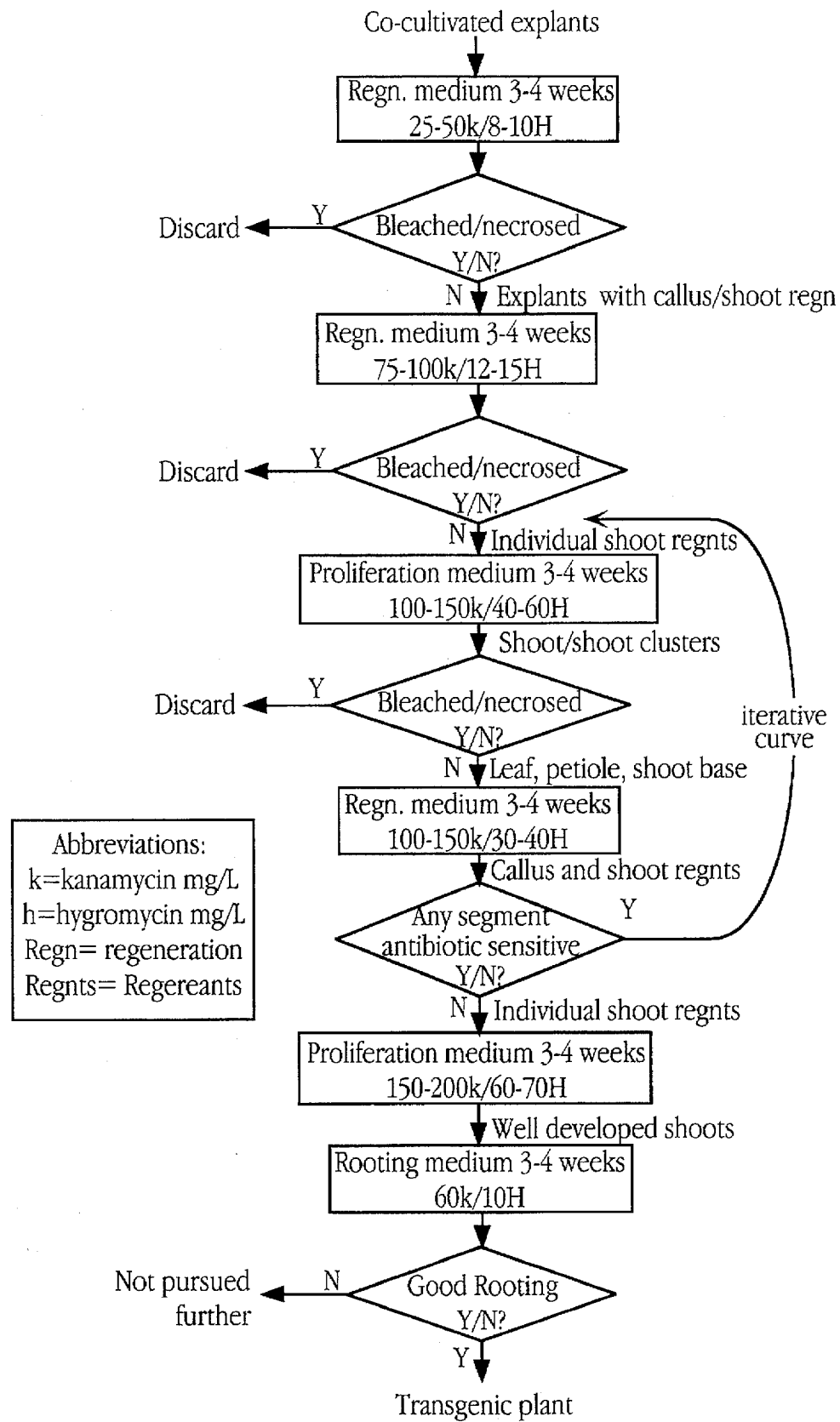
FIG. 13 is a flow chart outlining the transformation protocol for strawberry.

Shortly following co-cultivation, the segmented explants were exposed to 25–50 mg/l kanamycin, depending upon the plasmid (pAG5110, pAG5520, pAG1552) and the cultivar. As the explants underwent proliferation during the subculture interval of 3–4 weeks, the selection levels were gradually increased. The selection level was elevated to a maximum of 200 mg/l kanamycin in the case of shoot proliferation medium for the maintenance of transformants (FIG. 13).

The antibiotics kanamycin, geneticin (pAG5520) and hygromycin (pAG1452), were used as selection agents for cultivar Totem. The initial selection concentration of geneticin was 15 mg/l, elevated in a stepwise manner to a maximum of 40 mg/l. In the case of hygromycin, the initial concentration of selection agent was 10 mg/l, raised to a final level of 70 mg/l for maintenance of transformed shoots.

A portion of the explants in experiments ST10–ST14, as described in Example 11 and shown in Table 2, were cultured on screening medium containing 3–5 mg/l silver nitrate in order to evaluate the effects of silver nitrate on recovering transformants.

EXAMPLE 8

CHARACTERIZATION OF STRAWBERRY TRANSFORMANTS

A. HISTOCHEMICAL ASSAY FOR UIDA EXPRESSION Intact shoots (5–8 mm) and cut segments of the regenerants were subjected to 5-bromo-4-chloro-3-glucuronic acid (X-Gluc) treatment (Jefferson et al., 1987).

B. SOUTHERN HYBRIDIZATION

DNA isolated from transgenic and non-transformed strawberry plants were subjected to Southern hybridization analysis to confirm the presence of transgenes and to characterize the structure of the integrated DNA.

Genomic DNA was isolated from leaf tissue of transgenic and non-transformed control plants, as well as from greenhouse established plants (Doyle, et al., 1990). In a minor modification of the published procedure, polyvinylpolypyrrolidone (100 mg/g tissue) was added prior to addition of CTAB isolation buffer.

The DNA was digested with either EcoRI or EcoRI and HindIII. EcoRI cleaves the region between the borders of the binary vector once, and therefore produces junction fragments. The EcoRI and HindIII double digest produces a single intra-border 4.7kb SAMase fragment.

Complete digestion of the DNA was confirmed using a hybridization probe for the strawberry alcohol dehydrogenase gene, ADH (Wolyn, et al., 1990). The probe was also used as a relative measure of the DNA content in each lane.

EXAMPLE 9

ROOTING AND TRANSPLANTATION OF TRANSGENIC STRAWBERRY

Individual shoots (about 20–30 mm in length) isolated from multiple shoot clumps cultured on proliferation medium were cultured on rooting medium containing half strength MS (Murashige and Skoog, 1962) salts, B5 (Gamborg et al., 1968) vitamins, 1% sucrose, 100 mg/l carbenicillin, with selection agent.

The choice of selection agent was dependent upon the plasmid used in transformation. For shoots transformed with the plasmids, pAG5110, pAG5520 and pAG1552, 60 mg/l kanamycin or 15 mg/l geneticin was used. Shoots transformed with the plasmid, pAG1452, were cultured on rooting medium containing 10 mg/l hygromycin.

Inhibition experiments carried out on control non- transformed shoots revealed that kanamycin, at levels of 25 mg/l, and hygromycin, at levels of less than 5 mg/l, completely inhibited root formation.

Following storage in the greenhouse for about 2–4 days, well-rooted plants were rinsed to remove adherent media and potted in soil.

EXAMPLE 10

TRANSGENIC STRAWBERRY: CULTIVAR TRISTAR

Meristematic segments of cv. Tristar were transformed with the binary vector pAG5110 in either of the disarmed strains of A. tumefaciens, LBA4404 or EHA101, and cultured on regeneration medium containing either 0, 10 or 25 mg/l kanamycin. In about 3 weeks, formation of shoot initials from the meristematic segments was observed in each of the three treatments.

Explants from all three treatments were transferred to medium containing 50 mg/l kanamycin, followed by subsequent transfer to medium containing 75 mg/l kanamycin.

During periods of subculture, completely bleached tissues were discarded while fully or partially green tissues were maintained. Fully or partially green shoots were longitudinally segmented while transferring to fresh medium.

After 4 months of culture, the percent recovery of putative strawberry transformants consistently able to proliferate in the presence of selection agent exhibited a direct correlation to the level of selection in the initial screening medium. Exposure to zero level of selection during the first 3 weeks resulted in recovery of no or few putative transformants. Explants transformed with the binary vector pAG5110 in disarmed A. tumefaciens strain LBA4404 exhibited transformation frequencies for shoot regeneration of 0.0%, 2.3%, 13.6% for culture treatments in which the media contained 0, 10 and 25 mg/l kanamycin, respectively. Explants transformed with the binary vector pAG5110 in disarmed *A. tumefaciens* strain EHA101 exhibited transformation frequencies for shoot regeneration of 2.5%, 11.6% and 16.7%, corresponding to increasing levels of kanamycin, as described above.

Figure 6:
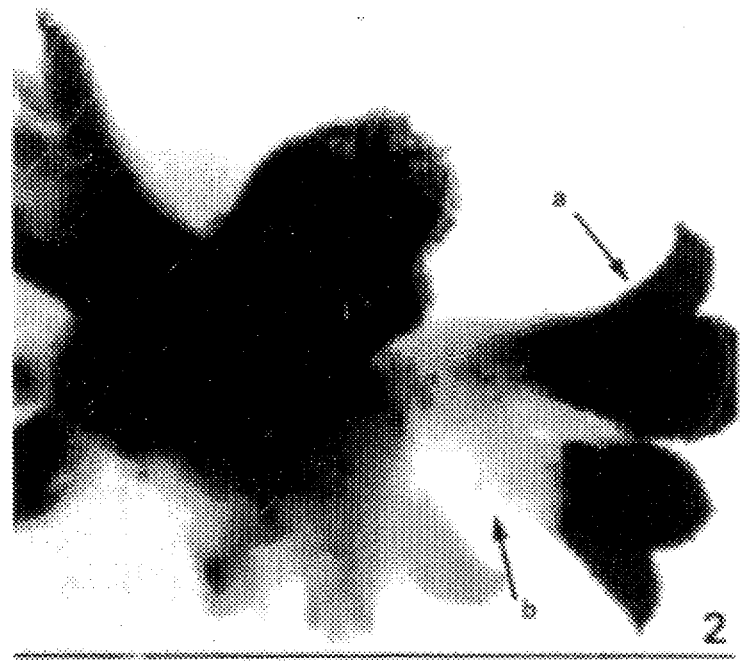
FIG. 6 represents shoot regenerants of cultivar Tristar transformed with pAG5110. Leaves are shown with (a) blue and (b) non-blue regions, on treatment with X-Gluc.
Figure 7:
FIG. 7 illustrates a cluster of shoots of cultivar Tristar transformed with pAG5110. The cluster contains both (a) completely blue shoots, and (b) shoots with some blue regions.

Histochemical analysis of regenerants on selection medium showed a mixture of completely blue shoots and shoots with some blue regions (FIGS. 6,7).

EXAMPLE 11

TRANSGENIC STRAWBERRY: CULTIVAR TOTEM

A. TRANSFORMATION AND PLANT REGENERATION.

Cultivar Totem was transformed with binary vectors containing DNA sequences encoding the SAMase gene and the selectable marker genes nptII or hpt (for resistance to kanamycin and hygromycin, respectively) in the disarmed A. tumefaciens strains EHA101 or EHA105, as described in Example 7.

Figure 8:
FIG. 8 shows leaf explants of cv. Totem undergoing shoot regeneration on selection medium containing 50 mg/l kanamycin. The non-transformed shoot on the right is bleached, indicating sensitivity to selection. The shoot on the left is resistant to selection and is green in color.

After co-cultivation, explants of cultivar Totem were cultured on regeneration medium containing either 50 mg/l kanamycin or 10 mg/l hygromycin, depending upon the plasmid used for transformation. After 3 weeks, bleached or necrotic tissues were discarded (FIG. 8). Explants with callus and/or shoot regenerants were segmented longitudinally and transferred to medium containing either 75 mg/l kanamycin or 15 mg/l hygromycin.

Initial explant identity was maintained for different segments. At the higher levels of selection agent, some segments were completely bleached or necrosed, while other segments were capable of withstanding the increased level of selection and produced shoot regenerants. Individual shoot regenerants were isolated and cultured on shoot proliferation medium containing 100–150 mg/l kanamycin or 40–50 mg/l hygromycin.

Figure 9:
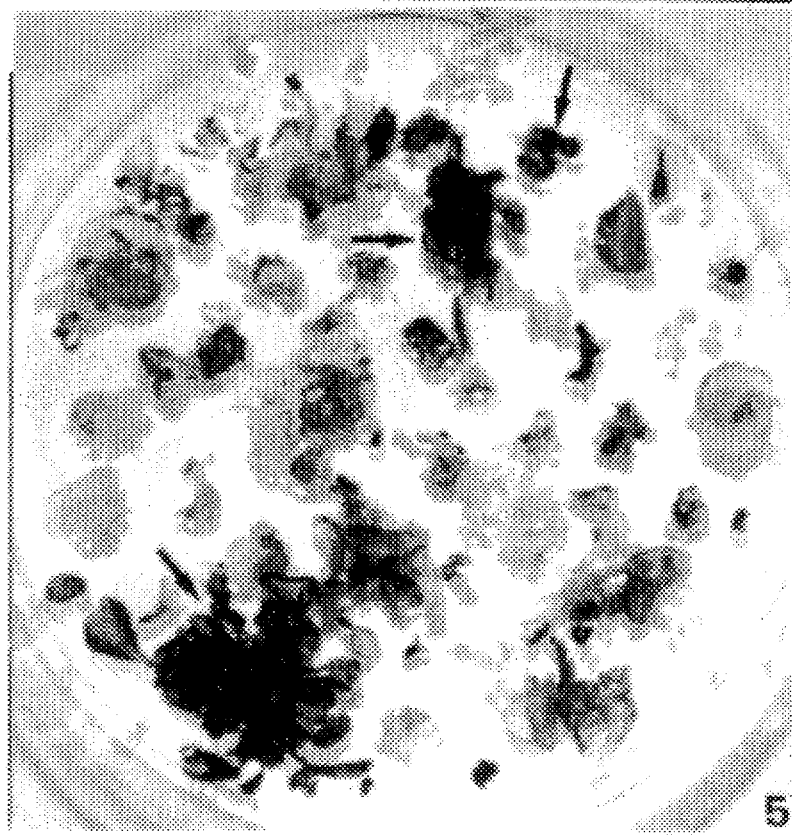
FIG. 9 shows explanted segments of a primary shoot regenerant of cultivar Totem on regeneration medium with 150 mg/l kanamycin. Segments capable of withstanding selection and capable of regeneration are indicated by arrows.

Petiole, leaf and shoot base explants were isolated from shoots exhibiting proliferation in the presence of increased levels of selection agent. The petiole, leaf and shoot base explants were recultured on regeneration medium containing 150 mg/l kanamycin or 40 mg/l hygromycin (FIG. 9).

If any of the segments of an event underwent bleaching or necrosis, the source regenerant was determined to be a chimera. Iterative culture was then continued until no part of the shoot regenerants showed sensitivity to selection (FIG. 13). Subsequent to screening to remove chimeric transformants, the regenerated shoots were multiplied on proliferation medium containing 200 mg/l kanamycin or 70 mg/l hygromycin, depending on the plasmid constructs.

A summary of the transformation frequencies from different experiments in cultivar Totem is provided in Table 2. In experiments ST10 through ST14 (Table 2), equal numbers of explants were screened on regeneration medium containing silver nitrate. In contrast to green compact callus and profuse shoot regenerants on silver nitrate-free screening medium, the explants on medium supplemented with silver nitrate produced friable yellow callus with occasional regenerants.

Figure 10:
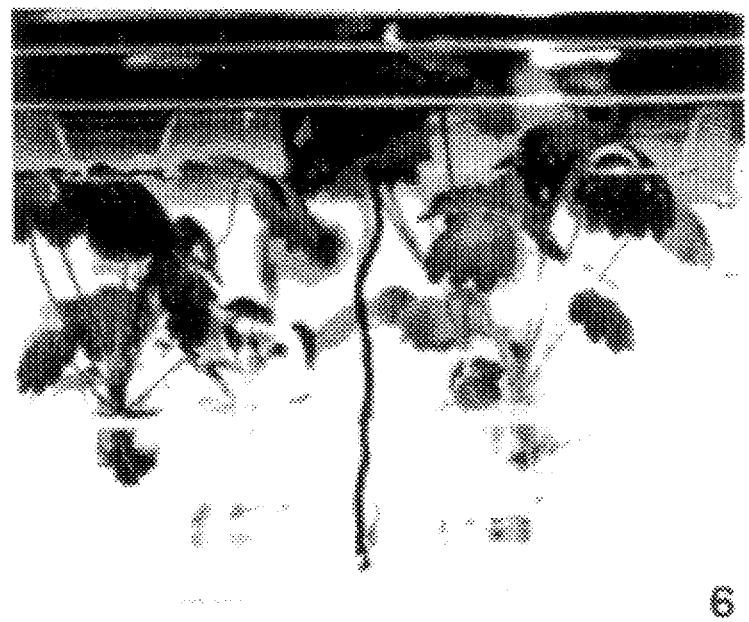
FIG. 10 shows rooted transgenic plants of cv. Totem on medium with 60 mg/l kanamycin, ready for outplanting to soil.
Figure 11:
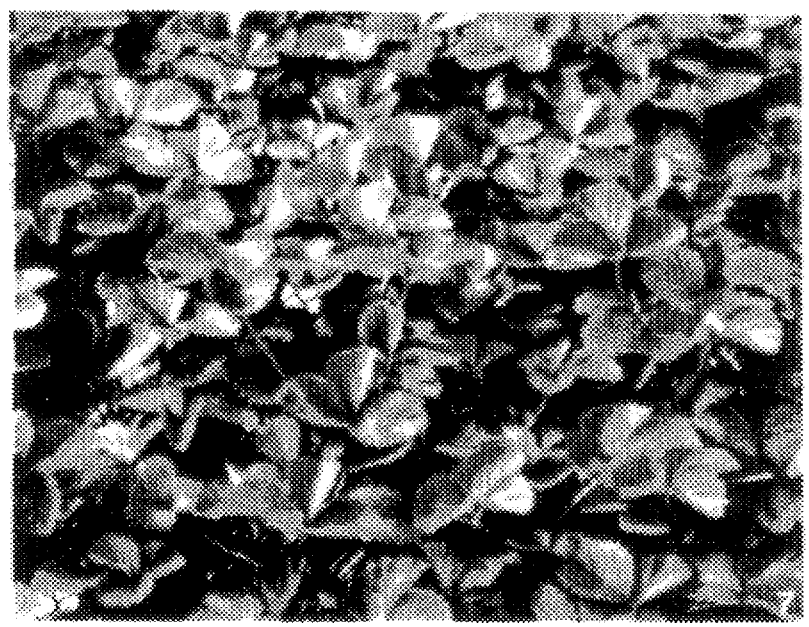
FIG. 11 shows transgenic plants of cv. Totem, established greenhouse.

Ninety five to 100% of the transgenic shoots successfully rooted on medium containing 60 mg/l kanamycin or 10 mg/l hygromycin (FIGS. 5 and 10, Table 2). Well-rooted transgenic plants were quickly established in soil with nearly 100 percent success (FIG. 11). The total duration of time from explant co-cultivation with *A.tumefaciens* to transfer of transgenics to soil was about 8–10 months.

TABLE 2

FREQUENCY OF TRANSFORMATION IN STRAWBERRY, CULTIVAR TOTEM

| Exper. ID | Agro strain/binary vector | Selection | Explants, # | | Trans. Freq. % | Trans. Events Recvr'd | Events Rooted |
|---|---|---|---|---|---|---|---|
| ST10-1A | EHA101/pAG5520 | Kanamycin | leaf | 31 | 35.5 | 11 | 11 |
|  |  |  | mer. seg. | 149 | 46.9 | 70 | 68 |
| ST11-1A | EHA105/pAG5520 | Kanamycin | leaf | 17 | 58.8 | 10 | 9 |
|  |  |  | mer. seg. | 147 | 40.8 | 60 | 59 |
| ST12-1 | EHA101/PAG5520 | Kanamycin | leaf | 40 | 32.5 | 13 | 13 |
| ST13-1 | EHA105/pAG4420 | Kanamycin | leaf | 40 | 12.5 | 5 | 4 |
| ST14-1 | EHA101/pAG5520 | Kanamycin | young shoot segments | 195 | 33.3 | 65 | 65 |
| ST20 | EHA105/pAG1452 | Hygromycin | young shoot segments | 1222 | 15.6 | 191 | 182 |

1. Trans. freq. = transformation frequency, see "Results" for definition.
2. Trans. events = Transformation events, see "Results" for definition.
3. Mer. seg. = Meristematic segment.

B. SOUTHERN HYBRIDIZATION

Southern blot data (FIGS. 12A–C) showed a variety of transgene copy numbers and integration structures. The DNA from transgenic plant leaves (plasmid pAG5520) was digested with either EcoRI alone or in conjunction with HindIII, as described in Example 8. The EcoRI digest allows determination of the number of individual integration events while the double digest allows an estimation of the total transgene copy number for that event.

Figures 12A, 12B, 12C:
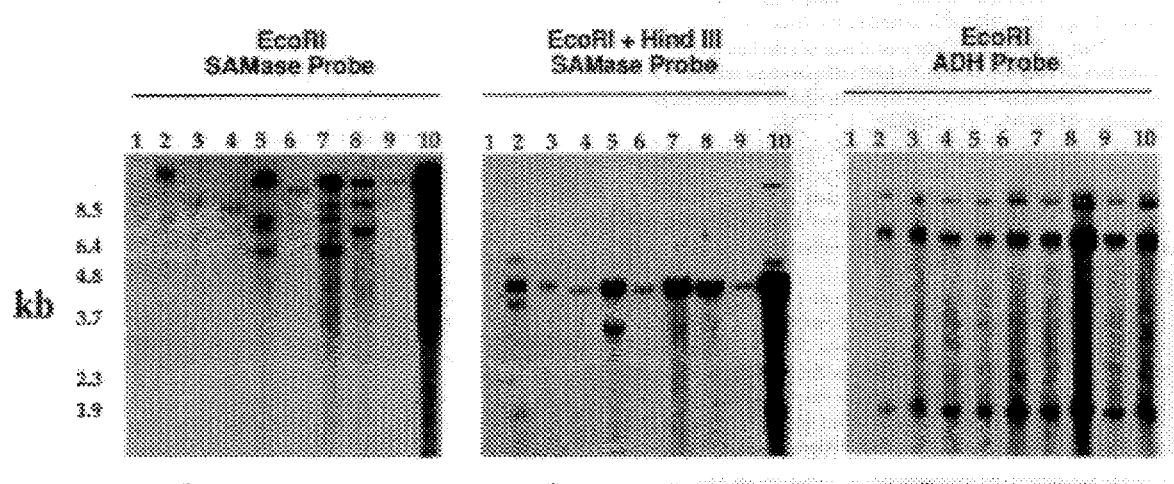
FIGS. 12A–12C show Southern hybridization blots of transformed cv. Totem (pAG5520). In the figures, lane 1, untransformed Totem, is compared to DNA from nine independent transformation events (lanes 2–10). DNAs were digested with either EcoRI alone (FIGS. 12A,C) or, in matching sequence, with both EcoRI and HindIII (FIG. 12B). The blots were probed with probes consisting of either SAMase alone (FIGS. 12A,B) or with SAMase and a putative strawberry alcohol dehydrogenase gene (FIG. 12C)

As seen in FIG. 12C, the last panel represents the EcoRI blot containing a hybridization probe for the strawberry alcohol dehydrogenase gene. The EcoRI blot indicates single integration events for lanes 4 and 6 and multiple events in lanes 5 and 7. The combined EcoRI and HindIII blot (FIG. 12B) confirms the multiple gene copy number for lanes 5 and 7 and indicates that an aberrant integration occurred in the event shown in lane 5 due to a smaller than expected fragment hybridizing to the SAMase probe. The signal strength in lanes 4 and 6 is identical to that of the EcoRI blot (FIG. 12A), confirming the single integration status for these two events. The differences in hybridization signal strength is not attributable to a difference in DNA amounts, since the EcoRI blot probed with the strawberry ADH gene showed similar signal intensities for lanes 4 through 7. The identical band pattern seen with the ADH probe clearly indicates complete digestion, validating the interpretation of multiple events for lanes 5 and 7.

A single integration event for strawberry (an octoploid) is expected to be eight-fold lower than for a native gene such as ADH. A comparison of the band intensities in lanes 4 and 6 for the SAMase-probed blots (FIGS. 12A,B) and the ADH probed blot (FIG. 12C) reveals a corresponding difference of approximately eight-fold.

EXAMPLE 12

IMPACT OF ANTIBIOTICS ON STRAWBERRY TRANSFORMANTS

In a separate experiment to examine the effects different antibiotics on the selection of transformants, leaf and petiole explants from cultivar Totem (transformed with the plasmid pAG1552) were co-cultivated with A.tumefaciens strain EHA105. The transformed explants were screened on medium supplemented with either kanamycin or geneticin.

The explants cultured on medium containing geneticin either became brown or produced scanty callus with poor rates of shoot regeneration (Table 3).

Transgenic shoots (confirmed by Southern hybridization), consistently prolific on medium containing kanamycin, were similarly cultured on geneticin-containing medium. The resulting explants, cultured in the presence of geneticin, exhibited a tendency for browning and declining proliferation with increasing passages.

Clonal transgenic shoots, capable of profuse rooting in the presence of 60 mg/l kanamycin, did not root on medium containing 15 mg/l geneticin.

TABLE 3

EFFECT OF KANAMYCIN vs. GENETICIN ON RECOVERY OF TRANSFORMANTS IN CV. TOTEM

| Exper. ID | Agro strain/binary vector | Selection | Explant, | # | Trans. Freq. % | Trans. Events Recvr'd |
|---|---|---|---|---|---|---|
| ST21-1 | EHA105/pAG1552 | Kanamycin | leaf | 329 | 15.5 | 51 |
|  |  | Kanamycin | petiole | 131 | 16.0 | 21 |
| ST21-2 | EHA105/pAG1552 | Geneticin | leaf | 293 | 1.3 | 4 |
|  |  | Geneticin | petiole | 132 | 2.3 | 3 |

1. Trans. freq. = Transformation frequency, see "Results" for definition.
2. Trans. events = Transformation events, see "Results" for definition.

Taken together, these results suggest kanamycin is a superior selection agent when compared to geneticin for both shoot regeneration and rooting.

While the invention has been described with reference to specific methods and embodiments, it will be appreciated that various modifications and changes may be made without departing from the invention.

It is claimed:

1. A method for producing a stably transformed raspberry or strawberry plant, comprising:

(i) introducing into cells of explant tissue from a target raspberry or strawberry plant to be transformed, an expression vector containing a selectable marker gene operably linked to a plant compatible-promoter, (ii) culturing said tissues from (i) in selection media having a threshold concentration of selective agent effective to discriminate between plant cells transformed with the vector and non-transformed cells, based on their ability to grow in the media, (iii) selecting tissues based on their growth characteristics in the selection media, (iv) regenerating the selected tissues in the presence of a selective agent whose concentration is effective to discriminate between transformed and non-transformed plant cells, based on the cells's ability to produce regenerated tissue, (v) selecting transformed regenerated tissue generated in (iv), (vi) obtaining an explant from the selected, transformed regenerated tissue, and (vii) repeating steps (iv) and (v) at least one time, until stably transformed regenerated tissue is obtained, where step (vi) precedes each repeat cycle.

2. The method of claim 1, where the regenerated tissue in step (vii) is determined to be stably transformed by dividing the regenerated tissue into explants, culturing the explants, and verifying that the growth of all explants is resistant to the highest concentration of selective agent used in steps (ii) through (vii).

3. The method of claim 1, where said selectable marker gene is either an NPTII or an hpt gene.

4. The method of claim 1, where said plant is a red-raspberry plant.

5. The method of claim 4, where said explant is a petiole explant.

6. The method of claim 4, where said selective agent is hygromycin or geneticin.

7. The method of claim 1, where said plant is a strawberry plant.

8. The method of claim 1, where the vector further includes a DNA sequence operably linked to regulatory elements effective to allow expression of the sequence in plant cells.

9. The method of claim 8, where said DNA sequence encodes S-adenosylmethionine hydrolase.

10. A transgenic strawberry plant produced by the method of claim 9, wherein ethylene biosynthesis in fruit produced by said plant is reduced in comparison to wild-type fruit.

11. The method of claim 8, wherein said DNA sequence encodes a product selected from the group consisting of aminocyclopropane-1-carboxylic acid (ACC) deaminase, ACC oxidase antisense molecule, ACC synthase antisense molecule, ACC oxidase cosuppression molecule, and ACC synthase cosuppression molecule.

12. A transgenic strawberry fruit produced by the plant of claim 10.

13. A transgenic red raspberry plant produced by the method of claim 9, wherein ethylene biosynthesis in fruit produced by said plant is reduced in comparison to wild-type fruit.

14. A transgenic red raspberry fruit produced by the plant of claim 13.

15. The method of claim 1, which further comprises growing the stably transformed regenerated tissue of step (vii) to produce a plant bearing fruit and, recovering said fruit.

16. The method of claim 7, where said selective agent is kanamycin.

17. The method of claim 7, where said selectable marker gene is either an NPTII or an hpt gene.

18. The method of claim 1, where said explant tissue is selected from the group consisting of leaf, meristem, node and petiole.

19. The method of claim 1, where said selective agent is selected from the group consisting of hygromycin, geneticin, and kanamycin.

20. The method of claim 1, where the regenerating step in each repeat cycle of steps (iv) and (v) is carried out at a successively higher concentration of the selection agent.

* * * * *

UNITED STATES PATENT AND TRADEMARK OFFICE
CERTIFICATE OF CORRECTION

PATENT NO. : 5,750,870

DATED : 5/12/98

INVENTOR(S) : Helena V. Mathews, et al.

It is certified that error appears in the above-identified patent and that said Letters Patent is hereby corrected as shown below:

Column 6, line 31, delete "(not shown)";

Column 6, line 42, insert --(as indicated by arrows)-- after "regions";

Column 6, line 46, insert --, as indicated by arrows-- after "regions";

Signed and Sealed this

Ninth Day of February, 1999

*Acting Commissioner of Patents and Trademarks*

Attest:

*Attesting Officer*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 586 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO (vi) ORIGINAL SOURCE:
    (C) INDIVIDUAL ISOLATE: SAM-K (ix) FEATURE:
    (A) NAME/KEY: CDS
    (B) LOCATION: 66..521

(xi) SEQUENCE DESCRIPTION: SEQ ID NO:1:

```
ACAGCTATGA CCATGATTAC GCCAAGCTTG CATGCCTGCA GGTCGACTCT AGAGGATCCG        60

CCACC ATG GTT TTC ACT AAA GAG CCT GCG AAC GTC TTC TAT GTA CTG          107
      Met Val Phe Thr Lys Glu Pro Ala Asn Val Phe Tyr Val Leu
        1               5                  10

GTT TCC GCT TTC CGT TCT AAC CTC TGC GAT GAG GTG AAT ATG AGC AGA        155
Val Ser Ala Phe Arg Ser Asn Leu Cys Asp Glu Val Asn Met Ser Arg
 15              20                  25                  30

CAC CGC CAC ATG GTA AGC ACT TTA CGT GCC GCA CCG GGT CTT TAT GGC        203
His Arg His Met Val Ser Thr Leu Arg Ala Ala Pro Gly Leu Tyr Gly
                 35                  40                  45

TCC GTT GAG TCA ACC GAT TTG ACC GGG TGC TAT CGT GAG GCA ATC TCA        251
Ser Val Glu Ser Thr Asp Leu Thr Gly Cys Tyr Arg Glu Ala Ile Ser
             50                  55                  60

AGC GCA CCA ACT GAG GAA AAA ACT GTT CGT GTA CGC TAC AAG GAC AAA        299
Ser Ala Pro Thr Glu Glu Lys Thr Val Arg Val Arg Tyr Lys Asp Lys
         65                  70                  75

GCG CAG GCA CTC AAT GTT GCA CGC CTA GCT TGT AAT GAG TGG GAG CAA        347
Ala Gln Ala Leu Asn Val Ala Arg Leu Ala Cys Asn Glu Trp Glu Gln
     80                  85                  90

GAT TGC GTA CTG GTA TAC AAA TCA CAG ACT CAC ACG GCT GGT CTG GTG        395
Asp Cys Val Leu Val Tyr Lys Ser Gln Thr His Thr Ala Gly Leu Val
 95                 100                 105                 110

TAC GCT AAA GGT ATC GAC GGG TAT AAG GCT GAA CGT CTG CCG GGT AGT        443
Tyr Ala Lys Gly Ile Asp Gly Tyr Lys Ala Glu Arg Leu Pro Gly Ser
                115                 120                 125

TTC CAA GAG GTT CCT AAA GGC GCA CCG CTG CAA GGC TGC TTC ACT ATT        491
Phe Gln Glu Val Pro Lys Gly Ala Pro Leu Gln Gly Cys Phe Thr Ile
            130                 135                 140

GAT GAG TTC GGT CGC CGC TGG CAA GTA CAA TAAGTGTTAA ACTCAAGGTC          541
Asp Glu Phe Gly Arg Arg Trp Gln Val Gln
        145                 150

ATGCACGATG CGTGGCGGAT CGGGTACCGA GCTCGAATTC ACTGG                      586
```

(2) INFORMATION FOR SEQ ID NO:2:

(i) SEQUENCE CHARACTERISTICS:
       (A) LENGTH: 152 amino acids
       (B) TYPE: amino acid
       (D) TOPOLOGY: linear (ii) MOLECULE TYPE: protein (xi) SEQUENCE DESCRIPTION: SEQ ID NO:2:

```
Met Val Phe Thr Lys Glu Pro Ala Asn Val Phe Tyr Val Leu Val Ser
 1               5                  10                  15

Ala Phe Arg Ser Asn Leu Cys Asp Glu Val Asn Met Ser Arg His Arg
            20                  25                  30

His Met Val Ser Thr Leu Arg Ala Ala Pro Gly Leu Tyr Gly Ser Val
        35                  40                  45

Glu Ser Thr Asp Leu Thr Gly Cys Tyr Arg Glu Ala Ile Ser Ser Ala
    50                  55                  60

Pro Thr Glu Glu Lys Thr Val Arg Val Arg Tyr Lys Asp Lys Ala Gln
65                  70                  75                  80
```

| | | | | | | | | | | | | | |
|---|---|---|---|---|---|---|---|---|---|---|---|---|---|
|Ala|Leu|Asn|Val|Ala|Arg|Leu|Ala|Cys|Asn|Glu|Trp|Glu|Gln|Asp|Cys|
| | | |85| | | | |90| | | | |95| | |
|Val|Leu|Val|Tyr|Lys|Ser|Gln|Thr|His|Thr|Ala|Gly|Leu|Val|Tyr|Ala|
| | | |100| | | | |105| | | | |110| | |
|Lys|Gly|Ile|Asp|Gly|Tyr|Lys|Ala|Glu|Arg|Leu|Pro|Gly|Ser|Phe|Gln|
| | | |115| | | | |120| | | | |125| | |
|Glu|Val|Pro|Lys|Gly|Ala|Pro|Leu|Gln|Gly|Cys|Phe|Thr|Ile|Asp|Glu|
| | |130| | | |135| | | | |140| | | | |
|Phe|Gly|Arg|Arg|Trp|Gln|Val|Gln| | | | | | | | |
|145| | | | |150| | | | | | | | | | |

( 2 ) INFORMATION FOR SEQ ID NO:3:

( i ) SEQUENCE CHARACTERISTICS:
        ( A ) LENGTH: 2216 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Tomato E8 promoter region ( x i ) SEQUENCE DESCRIPTION: SEQ ID NO:3:

```
GAATTCATTT  TTGACATCCC  TAATGATATT  GTTCACGTAA  TTAAGTTTTG  TGGAAGTGAG      60
AGAGTCCAAT  TTTGATAAGA  AAAGAGTCAG  AAAACGTAAT  ATTTAAAAG   TCTAAATCTT     120
TCTACAAATA  AGAGCAAATT  TATTTATTTT  TTAATCCAAT  AAATATTAAT  GGAGGACAAA     180
TTCAATTCAC  TTGGTTGTAA  AATAAACTTA  AACCAATAAC  CAAAGANCTA  ATAAATCTGA     240
AGTGGAATTA  TTAAGGATAA  TGTACATAGA  CAATGAAGAA  ATAATAGGTT  CGATGAATTA     300
ATAATAATTA  AGGATGTTAC  AATCATCATG  TGCCAAGTAT  ATACACAATA  TTCTATGGGA     360
TTTATAATTT  CGTTACTTCA  CTTAACTTTT  GCGTAAATAA  AACGAATTAT  CTGATATTTT     420
ATAATAAAAC  AGTTAATTAA  GAACCATCAT  TTTTAACAAC  ATAGATATAT  TATTTCTAAT     480
AGTTTAATGA  TACTTTTAAA  TCTTTTAAAT  TTTATGTTTC  TTTTAGAAAA  TAAAAATTCA     540
AAAAAATTAA  ATATATTTAC  AAAAACTACA  ATCAAACACA  ACTTCATATA  TTAAAAGCAA     600
AATATATTTT  GAAAATTTCA  AGTGTCCTAA  CAAATAAGAC  AAGAGGAAAA  TGTACGATGA     660
GAGACATAAA  GAGAACTAAT  AATTGAGGAG  TCCTATAATA  TATAATAAAG  TTTATTAGTA     720
AACTTAATTA  TTAAGGACTC  CTAAAATATA  TGATAGGAGA  AAATGAATGG  TGAGAGATAT     780
TGGAAAACTT  AATAATTAAG  GATNTTAAAA  TATATGGTAA  AAGATAGGCA  AAGTATCCAT     840
TATCCCCTTT  TAACTTGAAG  TCTACCTAGG  CGCATGTGAA  AGGTTGATTT  TTGTCACGT      900
CATATAGCTA  TAACGTAAAA  AAAGAAAGTA  AAATTTTTAA  TTTTTTTTAA  TATATGACAT     960
ATTTTAAACG  AAATATAGGA  CAAAATGTAA  ATGAATAGTA  AAGGAAACAA  AGATTAATAC    1020
TTACTTTGTA  AGAATTTAAG  ATAAATTTAA  AATTTAATAG  ATCAACTTTA  CGTCTAGAAA    1080
GACCCATATC  TAGAAGGAAT  TTCACGAAAT  CGGCCCTTAT  TCAAAAATAA  CTTTTAAATA    1140
ATGAATTTTA  AATTTAAGA   AATAATATCC  AATGAATAAA  TGACATGTAG  CATTTTACCT    1200
AAATATTTCA  ACTATTTTAA  TCCAATATTA  ATTTGTTTTA  TTCCAACAA   TAGAAAGTCT    1260
TGTGCAGACA  TTTAATCTGA  CTTTTCCAGT  ACTAAATATT  AATTTCTGA   AGATTTTCGG    1320
```

| | | | | | | |
|---|---|---|---|---|---|---|
| GTTTAGTCCA | CAAGTTTTAG | TGAGAAGTTT | TGCTCAAAAT | TTTAGGTGAG | AAGGTTTGAT | 1380 |
| ATTTATCTTT | TGTTAAATTA | ATTTATCTAG | GTGACTATTA | TTTATTTAAG | TAGAAATTCA | 1440 |
| TATCATTACT | TTTGCCAACT | TGTAGTCATA | ATAGGAGTAG | GTGTATATGA | TGAAGGAATA | 1500 |
| AACAAGTTCA | GTGAAGTGAT | TAAAATAAAA | TATAATTTAG | GTGTACATCA | AATAAAAACC | 1560 |
| TTAAAGTTTA | GAAAGGCACC | GAATAATTTT | GCATAGAAGA | TATTAGTAAA | TTTATAAAAA | 1620 |
| TAAAAGAAAT | GTAGTTGTCA | AGTTGTCTTC | TTTTTTTGG | ATAAAAATAG | CAGTTGGCTT | 1680 |
| ATGTCATTCT | TTTACAACCT | CCATGCCACT | TGTCCAATTG | TTGACACTTA | ACTAATTAGT | 1740 |
| TTGATTCATG | TATGAATACT | AAATAATTTT | TTAGGACTGA | CTCAAATATT | TTTATATTAT | 1800 |
| CATAGTAATA | TTTATCTAAT | TTTAGGACC | ACTTATTACT | AAATAATAAA | TTAACTACTA | 1860 |
| CTATATTATT | GTTGTGAAAC | AACAACGTTT | TGGTTGTTAT | GATGAAACGT | ACACTATATC | 1920 |
| AGTATGAAAA | ATTCAAAACG | ATTAGTATAA | ATTATATTGA | AAATTTGATA | TTTTTCTATT | 1980 |
| CTTAATCAGA | CGTATTGGGT | TTCATATTTT | AAAAAGGGAC | TAAACTTAGA | AGAGAAGTTT | 2040 |
| GTTTGAAACT | ACTTTTGTCT | CTTTCTTGTT | CCCATTCTC | TCTTAGATTT | CAAAAAGTGA | 2100 |
| ACTACTTTAT | CTCTTTCTTT | GTTCACATTT | TATTTTATTC | TATTATAAAT | ATGGCATCCT | 2160 |
| CATATTGAGA | TTTTTAGAAA | TTATTCTAAT | CATTCACAGT | GCAAAGACC | ATGGAA | 2216 |

( 2 ) INFORMATION FOR SEQ ID NO:4:

( i ) SEQUENCE CHARACTERISTICS:
        ( A ) LENGTH: 2796 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: E4 tomato gene DNA ( i x ) FEATURE:
        ( A ) NAME/KEY: CDS
        ( B ) LOCATION: 1439..1774

( i x ) FEATURE:
        ( A ) NAME/KEY: exon
        ( B ) LOCATION: 1439..1774

( i x ) FEATURE:
        ( A ) NAME/KEY: CDS
        ( B ) LOCATION: 1859..2113

( i x ) FEATURE:
        ( A ) NAME/KEY: exon
        ( B ) LOCATION: 1859..2113

( i x ) FEATURE:
        ( A ) NAME/KEY: intron
        ( B ) LOCATION: 1775..1858

( x i ) SEQUENCE DESCRIPTION: SEQ ID NO:4:

| | | | | | | |
|---|---|---|---|---|---|---|
| GAATTCTCAA | TTGAGCCCAA | TTCAATCTCC | AATTCAACC | CGTTTTAAAA | CTTTTTATTA | 60 |
| AGATATGTTT | CTATATTGAA | AGTATGAATT | ATTATCTATT | TAACATCTTT | TAGGATTTAT | 120 |
| CTATCCATTT | GCTACTTTTT | TAACAAAAAA | TTCTTGAGTG | AAAATTCAAA | TTGTGATTAT | 180 |
| AAAAGTTAAA | TATCAATATG | TTAAATTATT | AAGATTAATC | GGGTCAAATT | GGCGGGTCAA | 240 |
| GGCCCAATTC | TTTTTAGCC | CATTTAAGCT | CAAAGTAAAC | TTGGGTGGGT | CAAGACCCAA | 300 |

| | | | | | |
|---|---|---|---|---|---|
| CTCGATTTCT | GTTCAACCCA | TTTTAATATT | TCTATTTTCA | ACCTAACCCG | CTCATTTGAT | 360
| ACCCCTACAA | ATATCATATT | TGTGTGTGAA | ATATTTTTG | GGCTGGAGAG | AGAGGCCCCG | 420
| AGGGGAGTGG | AGGGGTGGGG | TGGGGAGAGA | GAGCGAGAAA | GAGTGGAGAG | AGAAATTTGA | 480
| TATGAAATCC | TACATATATT | ACAGATTGTA | ATGTTCTAAA | CTATAACGAT | TTGTCATAAA | 540
| CACATATCAT | GGATTTGTCT | TTTTGTGTAA | TTTTCCCAAT | TGTAAATAGG | ACTTCGTTAT | 600
| TTGAAACTTG | AAAGTGAAGT | CACATAGATT | AAGTACAAAC | ATTAATTAAA | GACCGTGGTG | 660
| GAATGATAAA | TATTTATTTA | TCTTTAATTA | GTTATTTTTT | TGGGAGCTCT | TTATTCCAAT | 720
| GTGAGACTTT | TGCGACATAT | ATTCAAATTT | AATCGAATCA | CAATATGTAT | TAGATTGATA | 780
| AAAAAATAAT | TTTTTACAA | TGTTAGTTGA | GACTCATAAC | TTACTGCCTA | TTGGTAATCT | 840
| ATGACTCCTA | ATTCCTTAAT | TATTTAAATA | TATCATCTTG | ATCGTTAACA | AAGTAATTTC | 900
| GAAAGACCAC | GAGTAAGAAG | ACAAACGAGA | ATACCAAAAA | ATTCAAAAAT | TTAATGTGAT | 960
| TTGGTCAATC | GATCTACGTC | CATAAAGGAG | ATGAGTAATC | TACTATAAAT | ATGAGAGTAC | 1020
| AAAATACAGA | GAGAAACAAC | CTCAACTAAT | TCACTCGGAA | TACATGAGAA | GTTCACACAA | 1080
| GTGATAACGT | ATCAAACTTG | TGACCCACAC | TTTTCCCTCT | AACCAAAGCT | CTTAAAACTA | 1140
| TATTGTGAAT | GCTGATTAAG | TTAAACGAAA | CAGTCCTAAA | TCTTTTCCGT | CCTATGAGAA | 1200
| ACAAGATTAA | TCAATTCACA | ATTTTTTTAA | AAAGAAAAAC | CTGTAAGAAA | TTTAGGCAAA | 1260
| CAAAACCTAA | CACAAGTTTG | TTTTTGTTTT | TACTACCAAC | AAGAAATTCA | AATGGCAAAT | 1320
| GTATAACGCA | TCTTAGCTAA | TTATATGACC | AGATTCAGAT | TAATATACAT | CTTCACCCAT | 1380
| GCAATCCATT | TCTATATAAA | GAAACATACA | CGAACTTGAT | ATTATTAGAG | ATTGAGCA | 1438 |

| | | | | | | | | | | | | | | | |
|---|---|---|---|---|---|---|---|---|---|---|---|---|---|---|---|
| ATG | GAG | GGT | AAC | AAC | AGC | AGT | AGC | AAG | TCA | ACC | ACC | AAT | CCA | GCA | TTG | 1486
| Met | Glu | Gly | Asn | Asn | Ser | Ser | Ser | Lys | Ser | Thr | Thr | Asn | Pro | Ala | Leu |
| 1 | | | | 5 | | | | | 10 | | | | | 15 | |

| | | | | | | | | | | | | | | | |
|---|---|---|---|---|---|---|---|---|---|---|---|---|---|---|---|
| GAT | CCG | GAT | CTG | GAC | AGC | CCG | GAT | CAG | CCG | GGT | CTG | GAG | TTT | GCC | CAA | 1534
| Asp | Pro | Asp | Leu | Asp | Ser | Pro | Asp | Gln | Pro | Gly | Leu | Glu | Phe | Ala | Gln |
| | | 20 | | | | | 25 | | | | | 30 | | | |

| | | | | | | | | | | | | | | | |
|---|---|---|---|---|---|---|---|---|---|---|---|---|---|---|---|
| TTT | GCT | GCC | GGC | TGC | TTT | TGG | GGA | GTC | GAA | TTG | GCT | TTC | CAG | AGG | GTT | 1582
| Phe | Ala | Ala | Gly | Cys | Phe | Trp | Gly | Val | Glu | Leu | Ala | Phe | Gln | Arg | Val |
| | | 35 | | | | | 40 | | | | | 45 | | | |

| | | | | | | | | | | | | | | | |
|---|---|---|---|---|---|---|---|---|---|---|---|---|---|---|---|
| GGA | GGA | GTA | GTG | AAG | ACG | GAG | GTT | GGG | TAC | TCT | CAG | GGG | AAT | GTC | CAT | 1630
| Gly | Gly | Val | Val | Lys | Thr | Glu | Val | Gly | Tyr | Ser | Gln | Gly | Asn | Val | His |
| | 50 | | | | | 55 | | | | | 60 | | | | |

| | | | | | | | | | | | | | | | |
|---|---|---|---|---|---|---|---|---|---|---|---|---|---|---|---|
| GAC | CCG | AAC | TAC | AAG | CTT | ATT | TGC | TCC | GGA | ACA | ACC | GAA | CAT | GCC | GAG | 1678
| Asp | Pro | Asn | Tyr | Lys | Leu | Ile | Cys | Ser | Gly | Thr | Thr | Glu | His | Ala | Glu |
| 65 | | | | 70 | | | | | 75 | | | | | 80 | |

| | | | | | | | | | | | | | | | |
|---|---|---|---|---|---|---|---|---|---|---|---|---|---|---|---|
| GCC | ATT | CGG | ATC | CAG | TTT | GAC | CCG | AAT | GTC | TGC | CCG | TAT | TCC | AAT | CTC | 1726
| Ala | Ile | Arg | Ile | Gln | Phe | Asp | Pro | Asn | Val | Cys | Pro | Tyr | Ser | Asn | Leu |
| | | | 85 | | | | | 90 | | | | | 95 | | |

| | | | | | | | | | | | | | | | |
|---|---|---|---|---|---|---|---|---|---|---|---|---|---|---|---|
| CTT | TCT | CTA | TTT | TGG | AGT | CGC | CAT | GAC | CCG | ACC | ACT | CTA | AAT | CGC | CAG | 1774
| Leu | Ser | Leu | Phe | Trp | Ser | Arg | His | Asp | Pro | Thr | Thr | Leu | Asn | Arg | Gln |
| | | | 100 | | | | | 105 | | | | | 110 | | |

| | | | | | |
|---|---|---|---|---|---|
| GTATCAAATT | CCTTTGGTGT | TTCATTTTAT | GTGATTAATA | TTAAAAATTT | TTTATATAAA | 1834 |

| | | | | | | | | | |
|---|---|---|---|---|---|---|---|---|---|
| TGTCATGATG | ATGGTTGTTG | CTAG | GGT | AAT | GAT | GTG | GGA | AAG | CAA | TAC | CGC | 1885
| | | | Gly | Asn | Asp | Val | Gly | Lys | Gln | Tyr | Arg |
| | | | 1 | | | | 5 | | | | |

| | | | | | | | | | | | | | | | |
|---|---|---|---|---|---|---|---|---|---|---|---|---|---|---|---|
| TCA | GGA | ATA | TAT | TAC | TAT | AAT | GAT | GCT | CAG | GCT | CAA | CTG | GCA | AGG | GAG | 1933
| Ser | Gly | Ile | Tyr | Tyr | Tyr | Asn | Asp | Ala | Gln | Ala | Gln | Leu | Ala | Arg | Glu |
| | 10 | | | | 15 | | | | | 20 | | | | | 25 |

| | | | | | | | | | | | | | | | |
|---|---|---|---|---|---|---|---|---|---|---|---|---|---|---|---|
| TCG | TTA | GAA | GCT | AAG | CAG | AAG | GAA | TTT | ATG | GAT | AAG | AAA | ATT | GTC | ACT | 1981
| Ser | Leu | Glu | Ala | Lys | Gln | Lys | Glu | Phe | Met | Asp | Lys | Lys | Ile | Val | Thr |
| | | | 30 | | | | | 35 | | | | | 40 | | |

```
GAA ATT CTT CCT GCT AAG AGA TTT TAT AGA GCT GAA GAG TAT CAC CAG          2029
Glu Ile Leu Pro Ala Lys Arg Phe Tyr Arg Ala Glu Glu Tyr His Gln
             45                  50                  55

CAA TAT CTA GAG AAG GGT GGG GGC AGA GGT TGT AAG CAG TCG GCT GCA          2077
Gln Tyr Leu Glu Lys Gly Gly Gly Arg Gly Cys Lys Gln Ser Ala Ala
         60                  65                  70

AAG GGC TGC AAT GAC CCA ATA AGG TGC TAC GGT  TGACAGCAGA TCTTTGAATG       2130
Lys Gly Cys Asn Asp Pro Ile Arg Cys Tyr Gly
     75                  80                 85

TCATAGCAAC TACAAAGAA  CTTGTTAGAC  ATTTGCTGTC  TTGCTTCTTT  AAATTTGAAT     2190
AAACATGACA ATGATTCTTA TAACTACTTG  CTCTCTTGGA  TGGAATAACT  AGTTGTCGTA     2250
AAGTATTCTC CTCTTGCTAA TTATTATCTC  TCTTTATATG  GTACCTGCAA  TTTGTTGCTT     2310
TAGTTACAGA ATAATGGACG TCAATTCTAT  ATCTTAATTT  GTTTAAGTC   TTAAATGAGG     2370
TGGTTTGTGT TTGAAAGCAA TATCAAGCAT  AGTAATACCA  ATGATTTAGT  AGATGAACTT     2430
AATCAAATCA AATTCCAAAA TGCAGTCTAC  AAATTGACAA  CATGAAGTTA  AGTGTATCTT     2490
ATGTAAATTG ACATCTTTCC TAGTAGATGC  CTAATACTTT  TGTAAAGACT  AAAATAAGCA     2550
CAGATGAGGC TTGTGCATTT AACTTAGAGT  TCATCCTTAG  GTGTGGCTGC  AGGAGACCCT     2610
GTAGGGTTGC TTGAAGTCTT GATGGGGTAG  GAGGGTTGCA  TTGCTATACC  ACACAACCCC     2670
TCTTCAGCGT CAACCTTGCG CTGCATTCTA  ATGTATCCTT  TTTCTCCCCA  TTCAGCTCCC     2730
CATGAGTTCT TCACAATCCA GTATTTGGTT  CCATCGACGG  TTGTGCCATA  CCCCACAATA     2790
GCCACA                                                                   2796
```

( 2 ) INFORMATION FOR SEQ ID NO:5:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Glu Gly Asn Asn Ser Ser Ser Lys Ser Thr Thr Asn Pro Ala Leu
 1               5                  10                  15

Asp Pro Asp Leu Asp Ser Pro Asp Gln Pro Gly Leu Glu Phe Ala Gln
             20                  25                  30

Phe Ala Ala Gly Cys Phe Trp Gly Val Glu Leu Ala Phe Gln Arg Val
         35                  40                  45

Gly Gly Val Val Lys Thr Glu Val Gly Tyr Ser Gln Gly Asn Val His
     50                  55                  60

Asp Pro Asn Tyr Lys Leu Ile Cys Ser Gly Thr Thr Glu His Ala Glu
65                  70                  75                  80

Ala Ile Arg Ile Gln Phe Asp Pro Asn Val Cys Pro Tyr Ser Asn Leu
             85                  90                  95

Leu Ser Leu Phe Trp Ser Arg His Asp Pro Thr Thr Leu Asn Arg Gln
        100                 105                 110

Gly Asn Asp Val Gly Lys Gln Tyr Arg Ser Gly Ile Tyr Tyr Tyr Asn
        115                 120                 125

Asp Ala Gln Ala Gln Leu Ala Arg Glu Ser Leu Glu Ala Lys Gln Lys
    130                 135                 140

Glu Phe Met Asp Lys Lys Ile Val Thr Glu Ile Leu Pro Ala Lys Arg
145                 150                 155                 160

Phe Tyr Arg Ala Glu Glu Tyr His Gln Gln Tyr Leu Glu Lys Gly Gly
                165                 170                 175
```

Gly Arg Gly Cys Lys Gln Ser Ala Ala Lys Gly Cys Asn Asp Pro Ile
    180                 185                 190

Arg Cys Tyr Gly
    195

( 2 ) INFORMATION FOR SEQ ID NO:6:

( i ) SEQUENCE CHARACTERISTICS:
  ( A ) LENGTH: 1678 base pairs
  ( B ) TYPE: nucleic acid
  ( C ) STRANDEDNESS: double
  ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
  ( C ) INDIVIDUAL ISOLATE: E4 tomato promoter /
   AdoMetase gene DNA ( i x ) FEATURE:
  ( A ) NAME/KEY: CDS
  ( B ) LOCATION: 1174..1629

( x i ) SEQUENCE DESCRIPTION: SEQ ID NO:6:

| | | | | | |
|---|---|---|---|---|---|
| AAGCTTAAAG | TAAACTTGGG | TGGGTCAAGA | CCCAACTCGA | TTTCTGTTCA | ACCCATTTTA | 60 |
| ATATTTCTAT | TTTCAACCTA | ACCCGCTCAT | TTGATACCCC | TACAAATATC | ATATTTGTGT | 120 |
| GTGAAATATT | TTTTGGGCTG | GAGAGAGAGG | CCCCGAGGGG | AGTGGAGGGG | TGGGGTGGGG | 180 |
| AGAGAGAGCG | AGAAAGAGTG | GAGAGAGAAA | TTTGATATGA | AATCCTACAT | ATATTACAGA | 240 |
| TTGTAATGTT | CTAAACTATA | ACGATTTGTC | ATAAACACAT | ATCATGGATT | TGTCTTTTTG | 300 |
| TGTAATTTTC | CCAATTGTAA | ATAGGACTTC | GTTATTTGAA | ACTTGAAAGT | GAAGTCACAT | 360 |
| AGATTAAGTA | CAAACATTAA | TTAAAGACCG | TGGTGGAATG | ATAAATATTT | ATTTATCTTT | 420 |
| AATTAGTTAT | TTTTTTGGGA | GCTCTTTATT | CCAATGTGAG | ACTTTTGCGA | CATATATTCA | 480 |
| AATTTAATCG | AATCACAATA | TGTATTAGAT | TGATAAAAAA | ATAATTTTTT | TACAATGTTA | 540 |
| GTTGAGACTC | ATAACTTACT | GCCTATTGGT | AATCTATGAC | TCCTAATTCC | TTAATTATTT | 600 |
| AAATATATCA | TCTTGATCGT | TAACAAAGTA | ATTTCGAAAG | ACCACGAGTA | AGAAGACAAA | 660 |
| CGAGAATACC | AAAAAATTCA | AAAATTTAAT | GTGATTTGGT | CAATCGATCT | ACGTCCATAA | 720 |
| AGGAGATGAG | TAATCTACTA | TAAATATGAG | AGTACAAAAT | ACAGAGAGAA | ACAACCTCAA | 780 |
| CTAATTCACT | CGGAATACAT | GAGAAGTTCA | CACAAGTGAT | AACGTATCAA | ACTTGTGACC | 840 |
| CACACTTTTC | CCTCTAACCA | AAGCTCTTAA | AACTATATTG | TGAATGCTGA | TTAAGTTAAA | 900 |
| CGAAACAGTC | CTAAATCTTT | TCCGTCCTAT | GAGAAACAAG | ATTAATCAAT | TCACAATTTT | 960 |
| TTTAAAAAGA | AAAACCTGTA | AGAAATTTAG | GCAAACAAAA | CCTAACACAA | GTTTGTTTTT | 1020 |
| GTTTTTACTA | CCAACAAGAA | ATTCAAATGG | CAAATGTATA | ACGCATCTTA | GCTAATTATA | 1080 |
| TGACCAGATT | CAGATTAATA | TACATCTTCA | CCCATGCAAT | CCATTCTAT | ATAAAGAAAC | 1140 |
| ATACACGAAC | TTGATATTAT | TAGAGATTGA | GCC ATG GTT TTC ACT AAA GAG CCT | | | 1194 |

```
                                          Met Val Phe Thr Lys Glu Pro
                                           1               5
GCG AAC GTC TTC TAT GTA CTG GTT TCC GCT TTC CGT TCT AAC CTC TGC    1242
Ala Asn Val Phe Tyr Val Leu Val Ser Ala Phe Arg Ser Asn Leu Cys
         10                  15                  20
GAT GAG GTG AAT ATG AGC AGA CAC CGC CAC ATG GTA AGC ACT TTA CGT    1290
Asp Glu Val Asn Met Ser Arg His Arg His Met Val Ser Thr Leu Arg
```

| | | | | | | | | | | | | | | | | |
|---|---|---|---|---|---|---|---|---|---|---|---|---|---|---|---|---|
| | | 25 | | | | 30 | | | | | 35 | | | | | |
| GCC | GCA | CCG | GGT | CTT | TAT | GGC | TCC | GTT | GAG | TCA | ACC | GAT | TTG | ACC | GGG | 1338 |
| Ala | Ala | Pro | Gly | Leu | Tyr | Gly | Ser | Val | Glu | Ser | Thr | Asp | Leu | Thr | Gly | |
| 40 | | | | | 45 | | | | 50 | | | | | 55 | | |
| TGC | TAT | CGT | GAG | GCA | ATC | TCA | AGC | GCA | CCA | ACT | GAG | GAA | AAA | ACT | GTT | 1386 |
| Cys | Tyr | Arg | Glu | Ala | Ile | Ser | Ser | Ala | Pro | Thr | Glu | Glu | Lys | Thr | Val | |
| | | | | 60 | | | | | 65 | | | | | 70 | | |
| CGT | GTA | CGC | TAC | AAG | GAC | AAA | GCG | CAG | CCA | CTC | AAT | GTT | GCA | CGC | CTA | 1434 |
| Arg | Val | Arg | Tyr | Lys | Asp | Lys | Ala | Gln | Pro | Leu | Asn | Val | Ala | Arg | Leu | |
| | | | 75 | | | | | 80 | | | | | 85 | | | |
| GCT | TCT | AAT | GAG | TGG | GAG | CAA | GAT | TGC | GTA | CTG | GTA | TAC | AAA | TCA | CAG | 1482 |
| Ala | Ser | Asn | Glu | Trp | Glu | Gln | Asp | Cys | Val | Leu | Val | Tyr | Lys | Ser | Gln | |
| | | 90 | | | | | 95 | | | | | 100 | | | | |
| ACT | CAC | ACG | GCT | GGT | CTG | GTG | TAC | GCT | AAA | GGT | ATC | GAC | GGG | TAT | AAG | 1530 |
| Thr | His | Thr | Ala | Gly | Leu | Val | Tyr | Ala | Lys | Gly | Ile | Asp | Gly | Tyr | Lys | |
| 105 | | | | | 110 | | | | | 115 | | | | | | |
| GCT | GAA | CGT | CTG | CCG | GGT | AGT | TTC | CAA | GAG | GTT | CCT | AAA | GGC | GCA | CCG | 1578 |
| Ala | Glu | Arg | Leu | Pro | Gly | Ser | Phe | Gln | Glu | Val | Pro | Lys | Gly | Ala | Pro | |
| 120 | | | | | 125 | | | | 130 | | | | | 135 | | |
| CTG | CAA | GGC | TGC | TTC | ACT | ATT | GAT | GAG | TTC | GGT | CGC | CGC | TGG | CAA | GTA | 1626 |
| Leu | Gln | Gly | Cys | Phe | Thr | Ile | Asp | Glu | Phe | Gly | Arg | Arg | Trp | Gln | Val | |
| | | | | 140 | | | | | 145 | | | | | 150 | | |
| CAA | TAACGTGTTA | AACTCAAGGT | CATGCACGAT | GCGTGGCGGA | TCGGGTACC | | | | | | | | | | | 1678 |
| Gln | | | | | | | | | | | | | | | | |

(2) INFORMATION FOR SEQ ID NO:7:

(i) SEQUENCE CHARACTERISTICS:
        (A) LENGTH: 152 amino acids
        (B) TYPE: amino acid
        (D) TOPOLOGY: linear (ii) MOLECULE TYPE: protein (xi) SEQUENCE DESCRIPTION: SEQ ID NO:7:

| | | | | | | | | | | | | | | |
|---|---|---|---|---|---|---|---|---|---|---|---|---|---|---|
| Met | Val | Phe | Thr | Lys | Glu | Pro | Ala | Asn | Val | Phe | Tyr | Val | Leu | Val | Ser |
| 1 | | | | 5 | | | | | 10 | | | | | 15 | |
| Ala | Phe | Arg | Ser | Asn | Leu | Cys | Asp | Glu | Val | Asn | Met | Ser | Arg | His | Arg |
| | | | 20 | | | | | 25 | | | | | 30 | | |
| His | Met | Val | Ser | Thr | Leu | Arg | Ala | Ala | Pro | Gly | Leu | Tyr | Gly | Ser | Val |
| | | | 35 | | | | | 40 | | | | | 45 | | |
| Glu | Ser | Thr | Asp | Leu | Thr | Gly | Cys | Tyr | Arg | Glu | Ala | Ile | Ser | Ser | Ala |
| | 50 | | | | | 55 | | | | | 60 | | | | |
| Pro | Thr | Glu | Glu | Lys | Thr | Val | Arg | Val | Arg | Tyr | Lys | Asp | Lys | Ala | Gln |
| 65 | | | | | 70 | | | | | 75 | | | | | 80 |
| Pro | Leu | Asn | Val | Ala | Arg | Leu | Ala | Ser | Asn | Glu | Trp | Glu | Gln | Asp | Cys |
| | | | | 85 | | | | | 90 | | | | | 95 | |
| Val | Leu | Val | Tyr | Lys | Ser | Gln | Thr | His | Thr | Ala | Gly | Leu | Val | Tyr | Ala |
| | | | 100 | | | | | 105 | | | | | 110 | | |
| Lys | Gly | Ile | Asp | Gly | Tyr | Lys | Ala | Glu | Arg | Leu | Pro | Gly | Ser | Phe | Gln |
| | | | 115 | | | | | 120 | | | | | 125 | | |
| Glu | Val | Pro | Lys | Gly | Ala | Pro | Leu | Gln | Gly | Cys | Phe | Thr | Ile | Asp | Glu |
| | | 130 | | | | | 135 | | | | | 140 | | | |
| Phe | Gly | Arg | Arg | Trp | Gln | Val | Gln | | | | | | | | |
| 145 | | | | | 150 | | | | | | | | | | |

(2) INFORMATION FOR SEQ ID NO:8:

(i) SEQUENCE CHARACTERISTICS:
        (A) LENGTH: 225 base pairs (B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: raspberry E4 gene DNA (ix) FEATURE:
(A) NAME/KEY: CDS
(B) LOCATION: 1..213

(xi) SEQUENCE DESCRIPTION: SEQ ID NO:8:

```
GAG CTC AGG TTT CAG CGA GTG GCC GGT GTG GTC AAG ACC GAG GTT GGG      48
Glu Leu Arg Phe Gln Arg Val Ala Gly Val Val Lys Thr Glu Val Gly
 1               5                  10                  15

TAC TCC CAG GGC CAC GTC CAC GAT CCG AAT TAC AAA CTG GTC TGC TCC      96
Tyr Ser Gln Gly His Val His Asp Pro Asn Tyr Lys Leu Val Cys Ser
             20                  25                  30

GGA ACT ACC AAC CAT TCG GAG GTC GTT CGG GTC CAG TTC GAC CCG CAA     144
Gly Thr Thr Asn His Ser Glu Val Val Arg Val Gln Phe Asp Pro Gln
         35                  40                  45

GTC TAC CCA TAC TCG GAC CTG CTT TCC GTC TTT TGG TCT CGT CAT GAT     192
Val Tyr Pro Tyr Ser Asp Leu Leu Ser Val Phe Trp Ser Arg His Asp
     50                  55                  60

CCA ACG ACT GTC AAT CGC CAG GTATGGGGAT TG                           225
Pro Thr Thr Val Asn Arg Gln
 65                  70
```

(2) INFORMATION FOR SEQ ID NO:9:

(i) SEQUENCE CHARACTERISTICS:
(A) LENGTH: 71 amino acids
(B) TYPE: amino acid
(D) TOPOLOGY: linear (ii) MOLECULE TYPE: protein (xi) SEQUENCE DESCRIPTION: SEQ ID NO:9:

```
Glu Leu Arg Phe Gln Arg Val Ala Gly Val Val Lys Thr Glu Val Gly
 1               5                  10                  15

Tyr Ser Gln Gly His Val His Asp Pro Asn Tyr Lys Leu Val Cys Ser
             20                  25                  30

Gly Thr Thr Asn His Ser Glu Val Val Arg Val Gln Phe Asp Pro Gln
         35                  40                  45

Val Tyr Pro Tyr Ser Asp Leu Leu Ser Val Phe Trp Ser Arg His Asp
     50                  55                  60

Pro Thr Thr Val Asn Arg Gln
 65                  70
```

(2) INFORMATION FOR SEQ ID NO:10:

(i) SEQUENCE CHARACTERISTICS:
(A) LENGTH: 2708 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: RASPBERRY E4 GENE (ix) FEATURE:
(A) NAME/KEY: misc_feature
(B) LOCATION: 1468..1469
(D) OTHER INFORMATION: /note= "small sequencing gap of unknown size"

(xi) SEQUENCE DESCRIPTION: SEQ ID NO:10:

| | | | | | | |
|---|---|---|---|---|---|---|
| AAGCTTAATT | GAGATGATTA | GCCCAGACCC | AGCAGGATTA | GGCTTAATGG | TGGTCCATTT | 60 |
| GAGAAAAAGA | TTAAAAATGA | TGTCATAAAA | AAACNTGGTC | GBCAGGATTC | NAACCTGCGC | 120 |
| GGGCAAAGCC | ACATGATTTC | TAGTCATGCC | CGATAACCAC | TCCGGCACGA | CCACAATGAT | 180 |
| GCTACAATTG | CTTTGTTGTA | ATCATTAACT | TATGGTTGAG | TTTGATGCTG | ATTAATACTA | 240 |
| TTATGTTTCC | ATTAACTACT | TTTGAAGTAT | ACAAAATTAC | GAATTTATAA | CCAAATTTGA | 300 |
| GGTATAATAT | GCGAGAGCTA | CCTAAATTTT | TCTTACTTAA | TTTTAAAGTA | CATTCAAATT | 360 |
| CTGAATTTAT | ATTGTGTATA | GTCAGAAAAC | AATCTACATA | TTTAAACACA | TAAATTTCTC | 420 |
| ACGTTTATAA | TCAATTTTGT | CGGTTCCTGT | AATTTTCTA | AATAAAAAG | CAACCAAAAT | 480 |
| TGTGCATCAA | CTTATTACAT | ACCATGGGAA | ATGCAAACTT | CAAAACTTAT | GGACTCAAAG | 540 |
| GGTACATATC | TAAACTACAT | ATTGTCAGAT | TCTTCACTCT | TATTTCTTGA | GGGCCTCGAG | 600 |
| GCATTACCAA | CCAAATCCAA | AAATTGCTTT | CGAATCTCAA | TAAAAGGAT | AACCCCATGA | 660 |
| AAAGACGTG | GACGGCAGGA | TTCGAACCTG | CGCGCAGAGC | CCACATGATT | TCTAGTCATG | 720 |
| CCCGATAACC | ACTCCGGCAC | GTCCACTTCA | CTGTTAACGT | TTACAGTAAC | AAGTCACTAA | 780 |
| CTACTAATCA | ACATTAGCTC | AGGAAATCAA | AACTAGATTA | TTTACATTTA | CAACGACATG | 840 |
| TCGTTCGAAG | TAGTTGGTCT | GTATCTGAGT | AGCTTTGGCG | GGTAGATTCA | ATCGCATTTC | 900 |
| TGCATATAAA | ACTGATCCTC | CCTCTATCGC | CAAAGTCAAA | CTGAAAATGG | CTTCCACCAC | 960 |
| CACCAACAAC | CCAGCTCTAG | ACCCAGATTC | GGACACTCCG | GATAATCCGG | GTCACGAGTT | 1020 |
| TGCTCAATTC | GGATCCGGGT | GCTTCTGGGG | AGCCGAGCTC | AGGTTTCAGC | GAGTGGCCGG | 1080 |
| TGTGGTCAAG | ACCGAGGTTG | GGTACTCCCA | GGGCCACGTC | CACGATCCGA | ATTACAAACT | 1140 |
| GGTCTGCTCC | GGAACTACCA | ACCATTCGGA | GGTCGTTCGG | GTCCAGTTCG | ACCCGCAAGT | 1200 |
| CTACCCATAC | TCGGACCTGC | TTTCCGTCTT | TTGGTCTCGT | CATGATCCAA | CGACTGTCAA | 1260 |
| TCGCCAGGTA | TGGGGATTGG | GGACTTCTGT | TTTCATTTGA | ATTTTGATGC | TAAAAAATTT | 1320 |
| CTTGCTTTTT | CATACTACAC | AGTACACACA | AAAAGTTGTG | TTTTTTTCA | TTCTTTTAAA | 1380 |
| TAGTAGTTGG | AAAAGTGCTC | TTGGAGTTGA | AGAGTACTTC | AGTATTGCAT | ATGGTCTCAG | 1440 |
| TGAAATGATA | GTGATTATCA | TAAGGAGTTT | AAAGGCAGGA | TGCATTTGT | GTATGANTGA | 1500 |
| TTTTGGGTAG | AATATTTTG | GAACAGTTAA | AATTTATGGG | CTGCTGCACA | CTGGCTATGA | 1560 |
| ACAAATGTAT | AGCATTAAAG | TGCTTATGAC | AAATTCACAA | TTGTATATTA | GCAGCAGAGA | 1620 |
| CATTAAAGTT | TCTAAATGCC | TTTTAAGTAG | ATTGGAAAAA | AGTGCTTTTT | TTGGTTGAAG | 1680 |
| AAGCACATTC | ACTATTTGCC | TGTTAATGGA | ATTGGTAATG | ATGAATCACA | AGGATATTTG | 1740 |
| TGAATACAAG | CAGGATGCTT | TTAGTGTGCA | AGTGATCTTT | CGGAACATTT | AAAATCGTCA | 1800 |
| TAACAAAGGT | GTAACATAAG | AAGGCTTTGA | AATATTCTCA | ATTTCTCATT | GATTGAATGA | 1860 |
| ATTATGTGTT | AGGGTGGAGA | TGTGGGTACT | CAATATCGAT | CTGGAATATA | CTACTACAAC | 1920 |
| GAAACGCAGG | CCCGTCTAGC | ACAGGAATCA | AGGAAGCAA | AGCAACTGGA | GTTAAGGAT | 1980 |
| AAGAAGGTGG | TGACAGAGAT | TCTTCCAGCA | AAGAGGTTTT | ACAGGGCAGA | GGAGTACCAT | 2040 |

-continued

| | | | | | |
|---|---|---|---|---|---|
| CAGCAATATC | TCGCAAAGGG | AGGAGGTAAT | GGCAACAAAC | AATCTGCTGA | AAAAGGTTGC | 2100
| AATGATCCTA | TTCGATGCTA | TGGTTGAGAA | ACTAATGCAT | TATGCCATTA | TTAAAACTCT | 2160
| ACTGGTTTAC | TATGCAGAAA | CACCTATGTC | AGTTCAATTA | TACTGAAGGC | ACCAAAGTGT | 2220
| CATCTTAAAT | TATATGGCAA | TGTTTTACTC | GTTATGAATA | AAGGAGGTCC | AAGTCGACCA | 2280
| GATATGAACA | AATGAAATAT | TGCCATGTTA | ATTGGAATCC | AGTAGTAATT | AGGATTTGTT | 2340
| TTGGTGTATG | TACTCCGATA | TCAAGATATG | CAAATGATGC | ATTGTGTTTT | TATATATTGA | 2400
| CAAGTTCCAA | ATTATAGTAC | TTCGTATGTG | TTATGCGGTT | TAATTAGTGT | TGCTTACTTG | 2460
| AATGGTATAT | TACTATTATG | CTTAGTAGGA | ACTAGGAACT | AGGGAATATG | TTGTGATAGA | 2520
| GTTGTCCAAC | GAAATTTTTG | ACCAAAGTTA | TTTCATTGAA | TAAAAACTAC | AGTCTTAGAG | 2580
| ATACATCCAA | TTCTATAAAG | TGAAAGAAGC | AAATATTATT | TGTTCATGAG | GCTATGAGTC | 2640
| ATGAACTTTA | TGCTATAACC | GAAGCAACCT | CAGAAAAGTC | GAAGTAAATT | GTGTATTGTT | 2700
| TAGAGCTC | | | | | | 2708

(2) INFORMATION FOR SEQ ID NO:11:

(i) SEQUENCE CHARACTERISTICS:
        (A) LENGTH: 191 amino acids
        (B) TYPE: amino acid
        (C) STRANDEDNESS: double
        (D) TOPOLOGY: linear (ii) MOLECULE TYPE: protein (iii) HYPOTHETICAL: NO (iv) ANTI-SENSE: NO (vi) ORIGINAL SOURCE:
        (C) INDIVIDUAL ISOLATE: RASPBERRY E4 PROTEIN (xi) SEQUENCE DESCRIPTION: SEQ ID NO:11:

```
Met Ala Ser Thr Thr Asn Asn Pro Ala Leu Asp Pro Asp Ser Asp
 1               5                  10                  15

Thr Pro Asp Asn Pro Gly His Glu Phe Ala Gln Phe Gly Ser Gly Cys
            20                  25                  30

Phe Trp Gly Ala Glu Leu Arg Phe Gln Arg Val Ala Gly Val Val Lys
        35                  40                  45

Thr Glu Val Gly Tyr Ser Gln Gly His Val His Asp Pro Asn Tyr Lys
    50                  55                  60

Leu Val Cys Ser Gly Thr Thr Asn His Ser Glu Val Val Arg Val Gln
65                  70                  75                  80

Phe Asp Pro Gln Val Tyr Pro Tyr Ser Asp Leu Leu Ser Val Phe Trp
                85                  90                  95

Ser Arg His Asp Pro Thr Thr Val Asn Arg Gln Gly Gly Asp Val Gly
            100                 105                 110

Thr Gln Tyr Arg Ser Gly Ile Tyr Tyr Asn Glu Thr Gln Ala Arg
        115                 120                 125

Leu Ala Gln Glu Ser Lys Glu Ala Lys Gln Leu Glu Phe Lys Asp Lys
    130                 135                 140

Lys Val Val Thr Glu Ile Leu Pro Ala Lys Arg Phe Tyr Arg Ala Glu
145                 150                 155                 160

Glu Tyr His Gln Gln Tyr Leu Ala Lys Gly Gly Asn Gly Asn Lys
                165                 170                 175

Gln Ser Ala Glu Lys Gly Cys Asn Asp Pro Ile Arg Cys Tyr Gly
        180                 185                 190
```